United States Patent
Teply et al.

(10) Patent No.: US 9,932,339 B2
(45) Date of Patent: Apr. 3, 2018

(54) HELQUATS WITH HETEROAROMATIC SUBSTITUENTS, PREPARATION THEREOF, AND USE THEREOF AS G-QUADRUPLEX STABILIZERS

(71) Applicants: USTAV ORGANICKE CHEMIE A BIOCHEMIE AV CR, V.V.I., Praha (CZ); VYSOKA SKOLA CHEMICKO-TECHNOLOGICKA V PRAZE, Praha (CZ)

(72) Inventors: Filip Teply, Roztoky u Prahy (CZ); Miroslav Hajek, Praha (CZ); Erika Kuzmova, Bratislava (CZ); Jaroslav Kozak, Holesov (CZ); Veronika Komarkova, Zbiroh (CZ); Pavla Hubalkova, Vermerovice (CZ); Paul Eduardo Reyes-Gutierrez, Colonia Himno San Luis Potosi (MX); Michael Jirasek, Cesky Brod (CZ); Manoj R. Sonawane, Maharashtra (IN); Vishwas D. Joshi, Maharashtra (IN); Lukas Severa, Votice (CZ); Jana Novotna, Kolin (CZ)

(73) Assignees: USTAV ORGANICKE CHEMIE A BIOCHEMIE AV CR, V.V.I., Praha (CY); VYSOKA SKOLA CHEMICKO-TECHNOLOGICKA V PRAZE, Praha (CZ)

( * ) Notice: Subject to any disclaimer, the term of this patent is extended or adjusted under 35 U.S.C. 154(b) by 0 days.

(21) Appl. No.: 15/313,492

(22) PCT Filed: May 26, 2015

(86) PCT No.: PCT/CZ2015/000052
§ 371 (c)(1),
(2) Date: Nov. 22, 2016

(87) PCT Pub. No.: WO2015/180701
PCT Pub. Date: Dec. 3, 2015

(65) Prior Publication Data
US 2017/0096433 A1  Apr. 6, 2017

(30) Foreign Application Priority Data
May 29, 2014 (CZ) .................. PV2014-369

(51) Int. Cl.
C07D 471/22 (2006.01)
A61K 31/475 (2006.01)
A61P 35/00 (2006.01)

(52) U.S. Cl.
CPC .................. *C07D 471/22* (2013.01)

(58) Field of Classification Search
CPC .................................................. C07D 471/22
See application file for complete search history.

(56) References Cited

U.S. PATENT DOCUMENTS 9,340,543 B2 * 5/2016 Teply .................. C07D 401/10

FOREIGN PATENT DOCUMENTS

| WO | 03/097642 A1 | 11/2003 | |
| WO | 2010/118711 A2 | 10/2010 | |
| WO | WO-2010118711 A2 * | 10/2010 | ........... C07D 401/06 |

OTHER PUBLICATIONS

Reyes-Gutierrez et al. "Functional helquats: helical cationic dyes with marked, switchable chiroptical properties in the visible region" Chem. Commun. 2015, 51, 1583-1586 (Year: 2015).*
International Search Report for PCT/CZ2015/000052 filed May 26, 2015.
International Search Opinion for PCT/CZ2015/000052 filed May 26, 2015.
Evera L et al: "Highly modular assembly of cationic helical scaffolds: rapid synthesis of diverse helquats via differential quaternization", Tetrahedron, Elsevier Science Publishers, Amsterdam, NL, vol. 66, No. 19, May 8, 2010 (May 8, 2010), pp. 3537-3552.
Marco Franceschin et al: "Aromatic Core Extension in the Series of N-Cyclic Bay-Substituted Perylene G-Quadruplex Ligands: Increased Telomere Damage, Antitumor Activity, and Strong Selectivity for Neoplastic over Healthy Cells", ChemMedChem, vol. 7, No. 12, Oct. 24, 2012 (Oct. 24, 2012), pp. 2144-2154.

* cited by examiner

*Primary Examiner* — Amanda L Aguirre
(74) *Attorney, Agent, or Firm* — Notaro, Michalos & Zaccaria P.C.

(57) ABSTRACT

Helquat derivatives of general formula I, in which substituents $R^1$ and $R^2$ are independently selected from a group comprising H and $C_1$ to $C_4$ alkyl, up to three of $S^{1,2}$, $S^{1',2'}$, $S^{3,4}$ and $S^{3',4'}$ are present, each of $S^{1,2}$, $S^{1',2'}$, $S^{3,4}$ and $S^{3',4'}$ independently represents a linker consisting of a bivalent hydrocarbon chain having 3-6 carbon atoms, preferably hydrocarbon chain having 4 carbon atoms, and one to four atoms selected from the carbon atoms with the descriptor 2, 4, 2', and 4' are substituted with a substituent $R^3$ of general formula II, wherein $R^4$ is substituted or unsubstituted heteroaryl, $T^1$ and $T^2$ are independent linkers that bridge atoms $N^5$ with $C^8$ and $N^{5'}$ with $C^{8'}$, wherein $T^1$ and $T^2$ independently represent a bivalent hydrocarbon chain having 2-5 carbon atoms, preferably 2 or 3 carbon atoms; and anions $(X^1)^-$ and $(X^2)^-$ independently represent anions of pharmaceutically acceptable salts.

21 Claims, 1 Drawing Sheet

SEQUENCE LISTING

```
<160> NUMBER OF SEQ ID NOS: 4

<210> SEQ ID NO 1
<211> LENGTH: 26
<212> TYPE: DNA
<213> ORGANISM: Artificial
<220> FEATURE:
<223> OTHER INFORMATION: Sequence ds26 used in biological testing

<400> SEQUENCE: 1
caatcggatc gaattcgatc cgattg                                         26
```

```
<210> SEQ ID NO 2
<211> LENGTH: 21
<212> TYPE: DNA
<213> ORGANISM: Artificial
<220> FEATURE:
<223> OTHER INFORMATION: Sequence F21T used in biological testing

<400> SEQUENCE: 2
gggttagggt tagggttagg g                                         21

<210> SEQ ID NO 3
<211> LENGTH: 27
<212> TYPE: DNA
<213> ORGANISM: Artificial
<220> FEATURE:
<223> OTHER INFORMATION: Sequence Fmyc27T used in biological testing

<400> SEQUENCE: 3
tggggagggt ggggagggtg gggaagg                                   27

<210> SEQ ID NO 4
<211> LENGTH: 27
<212> TYPE: DNA
<213> ORGANISM: Artificial
<220> FEATURE:
<223> OTHER INFORMATION: Sequence c Myc27 used in biological testing

<400> SEQUENCE: 4
tggggagggt ggggagggtg gggaagg                                   27
```

HELQUATS WITH HETEROAROMATIC SUBSTITUENTS, PREPARATION THEREOF, AND USE THEREOF AS G-QUADRUPLEX STABILIZERS

FIELD OF THE INVENTION

The invention relates to new helquats with heteroaromatic substituents, to preparation thereof, and to use thereof as medicaments for treatment of diseases related to increased cellular proliferation and for stabilization of G-quadruplexes.

BACKGROUND ART

Original compounds useful in cancer therapy are subject of interest in industrial and academic laboratories.

Malignant tumor diseases are the most frequent cause of death. The uncontrolled cellular growth is linked to inherited genetic factors as well as environmental factors. For initiation and development of a malignant disease, the accumulation of several various genetic or epigenetic changes is necessary. This leads to transformation of a healthy cell into a fully malignant phenotype. Cumulation of gene mutations in genes encoding proteins taking part in the regulation of cell division and differentiation, in the control of DNA replication fidelity, in the regulation of apoptosis of the damaged cells, in intercellular communication and intracellular signaling pathways leads to perturbations in normal functioning of these proteins. Malignant cells, unlike benign cells, have the ability to penetrate into the surrounding healthy tissue (invasiveness). Cancer cells can be released from the original tumor and spread through the bloodstream or lymphatic system to distant parts of the body to form new tumors (metastatic process).

The aim of anticancer therapy is to selectively induce apoptosis in the undesirable cancer cells, while not affecting the surrounding healthy tissue. Cytotoxic therapeutics act through DNA damage or microtubule damage and their specificity towards tumor cells in human body is due to their ability to selectively kill fast-proliferating cells. This selectivity can be determined by their cytostatic effects in cell culture in vitro [Chabner B. A., Roberts T. G. (2005), *Nat. Rev. Cancer* 5, 65-72; Lüllmann H. et al. (2005), Farmakologie a toxikologie, Grada, 15th edition].

The fact that tumor cells are derived from cells of a host organism is a limiting factor for achieving the maximal selectivity of the cytotoxic effect. The sensitivity of cancer cells towards treatment is determined by the growth fraction of a tumor (the ratio of proliferating and non-proliferating tumor cells), the site of action of the cytostatic agent within the cell cycle, and the natural and the acquired resistance of the tumor cells against the cytostatics.

G-quadruplexes are regarded as attractive molecular targets of anticancer therapy of the future [Neidle S. (2011), Therapeutic Applications of Quadruplex Nucleic Acids, Academic Press, 1st edition]. Influencing the stability of DNA G-quadruplexes was identified as one of the regulatory mechanisms for key processes on cellular level. Original compounds useful in influencing the stability of G-quadruplexes are thus of interest for the industry and many academic laboratories. Frequent presence of G-quadruplexes was found in promoter regions of genes, and the physicochemical and structural characteristics of these DNA structures make them interesting therapeutic targets. Repression of oncogene transcription as a result of stabilization of these four-stranded DNA structures in promoter regions of genes using small molecules is thus one of the pursued strategies of anticancer therapy [Balasubramanian S. et al, (2011), *Nature Reviews Drug Discovery* 10, 261-275].

Telomeric ends of chromosomes are another area where G-quadruplexes play a key role [Neidle S. (2010), *FEBS Journal* 277, 1118-1125]. Human telomeres are nucleoprotein complexes containing repeating DNA sequence (5'GGGTTA3')$_n$ (n=100-4000), which has a single strand 24-400 base overhang on its 3'-end [Cimino-Reale G. et al. (2001) *Nucleic Acids Res.* 29, E35]. Telomeric DNA is gradually getting shorter with each cycle of cell division (so called end replication problem). This process determines the limit of overall number of divisions, which are possible in normal (non-cancer) cells. Majority of cancer cells overcome this end replication problem with help of telomerase mediated extension of telomeric DNA ends. Stabilization of G-quadruplexes in telomeres via small molecules can lead to efficient inhibition of telomerase activity and restoration of the limit for cell division.

Targeting of telomeric G-quadruplexes can influence the function of telomeres also by other means than via inhibition of telomerase. Ends of chromosomes are associated with wide range of proteins, which bind to them. This nucleoprotein complex (so called sheltering complex) is responsible for structural integrity of telomeres in vivo. Small molecules which bind in telomeric region can release proteins from sheltering complex and cause telomere destabilization. This process can lead to apoptosis or replicative senescence. Similar to targeting G-quadruplexes in gene promoters, targeting at telomeric ends of chromosome, which is rich in G-quadruplexes, is also a promising strategy of anticancer therapy.

Currently, small molecules are being sought to induce formation of G-quadruplex-ligand complexes. Such molecules could induce selective inhibition of cancer cell growth [Ou T.-M. et al. (2008), *ChemMedChem*, 3, 690-713; Phatak P. et al. (2007), *Br. J. Cancer*, 96, 1223-1233; Di Leva F. S. et al. (2013) *J. Med Chem.*, 56, 9646-54]. Example of such small organic molecule, which is used for G-quadruplex stabilization in vitro and in vivo, is TMPyP4 [Balasubramanian S. et al. (2011), *Nature Reviews Drug Discovery* 10, 261-275]. A significant drawback is the low selectivity of this particular compound towards G-quadruplex in presence of DNA duplex.

Presently, there are numerous G-quadruplex stabilizers, out of which a few have been tested clinically. In spite of the fact that these compounds limited growth of cancer cells in a promising way, neither has been introduced in clinical practice. For example quarfloxin had poor bioavailability [Quarfloxin (CX-3543); Phase II clinical trials; ClinicalTrials.gov; NCT00780663]. Development of new G-quadruplex stabilizers is a field of research which still receives great attention. Particularly desirable are original small molecules, which are effective in repression of oncogene transcription and, at the same time, show acceptable level of side effects during their applications.

This invention opens a straightforward way for obtaining a brand new class of compounds, which are useful as medicaments for diseases related to increased cellular proliferation and stabilization of G-quaduplexes. These compounds structurally belong to the family of helquats, organic cations based on quaternary nitrogen atom, for which also a non-therapeutic use has been suggested, such as sensitizers for photography [Tani T. (1995) Photographic Sensitivity, Theory and Mechanisms, OUP, Oxford].

Helical extended diquats (helquats) [Adriaenssens et al. (2009), *Chem. Eur. J.* 15, 1072-1076; Severa et al. (2010), Tetrahedron 66, 3537-3552; Vávra et al. (2012), Eur. J. Org. Chem. 489-499] represent a new and nearly unexplored class of compounds with dicationic helical skeleton. The described basic helquat skeletons are built around two quaternary N-heteroaromatic units, which introduce into this structure two positively charged centers, for example in the form of pyridinium, quinolinium or isoquinolinium cationic units. To this end, the whole arrangement of a typical helquat is associated with dicationicity as well as helical chirality, which is a combination that has not been studied before in the context of small aromatic organic molecules.

Previous efforts focused on helquats allowed only a limited variability of structures which was caused by the fact that each prepared compound was build using multistep synthesis de novo [PV 2009-237]. The follow-up patent application (PV 2013-32, PCT/CZ2014/000009) introduced not only new helquat derivatives but also preparation thereof via one-step diversification of methyl-substituted helquats using Knoevenagel condensation with arylaldehydes.

The present invention describes a completely new class of helquats, which is distinguished by the presence of heteroaryl substituent(s). These compounds are prepared again via one-step diversification of the methyl-substituted helquats using Knoevenagel condensation, but now with substituted or non-substituted heteroarylaldehydes.

DISCLOSURE OF THE INVENTION

The object of the present invention are helquat derivatives of the general formula I (I)

wherein
substituents $R^1$ and $R^2$ are independently selected from the group comprising H and $C_1$ to $C_4$ alkyl; up to three of $S^{1,2}$, $S^{1',2'}$, $S^{3,4}$ and $S^{3',4'}$ linkers are present,
each of $S^{1,2}$, $S^{1',2'}$, $S^{3,4}$ and $S^{3',4'}$ independently represents a linker consisting of a bivalent hydrocarbon chain having 3-6 carbon atoms, preferably hydrocarbon chain having 4 carbon atoms, more preferably hydrocarbon chain having 4 carbon atoms and two double bonds, or $S^{1,2}$, $S^{1',2'}$, $S^{3,4}$ and $S^{3',4'}$ are not present; and
from one to four atoms selected from the carbon atoms with the descriptor 2, 4, 2', and 4' (the carbon atom must be free of the S-linker as would be apparent to a person skilled in the art) are substituted with a substituent $R^3$ of general formula II (II)

wherein
$R^4$ is substituted or unsubstituted heteroaryl,
$T^1$ and $T^2$ are independent linkers that bridge atoms $N^5$ with $C^8$ and $N^{5'}$ with $C^{8'}$, wherein $T^1$ and $T^2$ independently represent a bivalent hydrocarbon chain having 2-5 carbon atoms, preferably 2 or 3 carbon atoms,
wherein heteroaryl is an aromatic carbocyclic group containing:
4 to 26 and preferably 4 to 12 carbon atoms, and at least one aromatic ring or multiple aromatic rings (condensed or non-condensed), wherein at least one carbon atom of the ring is replaced with a heteroatom selected from a group comprising N, S and O; the heteroaryl can be unsubstituted or substituted with 1 to 5 substituents selected from a group comprising $C_1$ to $C_6$ alkyl, $C_3$ to $C_{12}$ cycloalkyl (condensed or non-condensed) optionally having at least one carbon atom of the ring replaced with a heteroatom selected from a group comprising N, S and O; $C_6$ to $C_{16}$ (preferably $C_6$ to $C_{12}$) aryl, $C_6$ to $C_{26}$ (preferably $C_6$ to $C_{12}$) arylalkyl, $C_1$ to $C_6$ halogenoalkyl, $C_1$ to $C_{12}$ alkoxy, $C_6$ to $C_{16}$ (preferably $C_6$ to $C_{12}$) aryloxy, benzyloxy, $C_1$ to $C_6$ alkylthio, $C_6$ to $C_{16}$ (preferably $C_6$ to $C_{12}$) arylthio, halogeno, —OH, —SH, —NH$_2$, $C_1$ to $C_6$ alkylamino, $C_6$ to $C_{16}$ (preferably $C_6$ to $C_{12}$) arylamino, $C_1$ to $C_6$ acylamino, —CN, nitro, —SO$_3$H, —COOR$_n$, —C(=O)N(R$_n$)$_2$, wherein R$_n$ is hydrogen or $C_1$ to $C_6$ alkyl or $C_6$ to $C_{16}$ (preferably $C_6$ to $C_{12}$) aryl;
and anions $(X^1)^-$ and $(X^2)^-$ independently represent anions of salts, in particular of pharmaceutically acceptable salts.

The salts include salts with alkali metals, salts with inorganic or organic anions and in particular, but not exclusively, pharmaceutically acceptable salts suitable for physiological application.

Pharmaceutically acceptable salts can be salts derived from inorganic or organic acids. Expert in the field will be able to determine, which salts are pharmaceutically acceptable; especially salts having one or more favourable physico-chemical characteristic such as longer pharmaceutical stability at various temperatures and humidities, desired solubility in water or oil, or are not toxic. Suitable pharmaceutically acceptable salts of the compounds according to this invention preferably include anions derived from inorganic acids such as hydrochloric acid, hydrobromic acid, hydrofluoric acid, boric acid, phosphoric acid, metaphosphoric acid, nitric acid, carbonic acid, sulfurous acid, sulphuric acid; and organic acids such as acetic acid, benzenesulfonic acid, benzoic acid, citric acid, ethanesulfonic acid, fumaric acid, gluconic acid, glycolic acid, isethionic acid, lactic acid, laktobionic acid, maleic acid, malonic acid, methanesulfonic acid, trifluoromethanesulfonic acid, succinic acid, toluenesulfonic acid, tartaric acid, and trifluoroacetic acid. Suitable organic acids generally encompass for example the following classes of organic acids: aliphatic, cycloaliphatic, aromatic, arylaliphatic, heterocyclic, carboxylic and sulfonic acids. Specific examples of suitable organic acid salts include acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, pamoate, methanesulfonate, ethanesulfonate, benzenesulfonate, pantothenate, toluenesulfonate, 2-hydroxyethanesulfonate, sulfanilate, cyclohexylaminosulfonate, 3-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalenesulfonate, oxalate, palmoate, pectinate, 3-phenylpropionate, picrate, pivalate, thiocyanate and undecanoate.

The object of the invention are preferably the following helquat derivatives:

2,4-bis((E)-2-(thiophen-3-yl)vinyl)-6,7,10,11-tetrahydrodipyrido[2,1-a:1',2'-k][2,9]phenanthroline-5,12-diium trifluoromethanesulfonate, i.e. HTA-C5-9

(E)-2-(2-(dibenzo[b,d]furan-4-yl)vinyl)-6,7,10,11-tetrahydrodipyrido[2,1-a:1',2'-k][2,9]phenanthroline-5,12-diium trifluoromethanesulfonate, i.e. LSA-C13-8

(E)-13-(2-(5-(ethoxycarbonyl)-1H-pyrrol-3-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. MJA-C8-28

(E)-13-(2-(5-bromo-1H-indol-3-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. MJA-C9-30

2,13-bis((E)-2-(5-bromothiophen-2-yl)vinyl-8,9-dimethyl-6,7,10,11-tetrahydrodipyrido[2,1-a: 1',2'-k][2,9]phenanthroline-5,12-diium trifluoromethanesulfonate, i.e. MJB-C5-3

2,13-bis((E)-2-(2,6-dimethoxypyridin-3-yl)vinyl)-8,9-dimethyl-6,7,10,11-tetrahydrodipyrido[2,1-a:1',2'-k][2,9]phenanthroline-5,12-diium trifluoromethanesulfonate, i.e. MJB-C8-27

19-((E)-2-(1-methyl-1H-indol-2-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, i.e. MSC-C10-10

19-((E)-2-(2-methyl-1H-indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, i.e. MSC-C10-11

19-((E)-2-(1H-benzo[g]indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, i.e. MSC-C13-16

19-((E)-2-(2-phenyl-1H-indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, i.e. MSC-C15-8

19-((E)-2-(1H-indol-5-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, i.e. MSC-C9-10

19-((E)-2-(5-bromo-1H-indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, i.e. MSC-C9-30

4,15-bis((E)-4-(pyridin-2-yl)styryl)-6,7,8,11,12,13-hexahydrodipyrido[1,2-a:1',2'-a']benzo[2,1-c:3,4-c']bisazepindiium trifluoromethanesulfonate, i.e. PRA-C12-5

2,4,15,17-tetra((E)-2-(1-methyl-1H-indol-2-yl)vinyl)-6,7,8,11,12,13-hexahydrodipyrido[1,2-a:1',2'-a']benzo[2,1-c:3,4-c']bisazepindiium trifluoromethanesulfonate, i.e. PRC-C10-10

(E)-11-(2-([2,2';5',2''-terthiophen]-5-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. VDJA-C13-6

(E)-11-(2-(dibenzo[b,d]furan-4-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. VDJA-C13-8

2,15-bis((E)-2-(2,6-dimethoxypyridin-3-yl)vinyl)-6,7,10,11-tetrahydrodipyrido[2,1-a:1',2'-k][2,9]phenanthroline-5,12-diium trifluoromethanesulfonate, i.e. PDA-C8-27

(E)-2-(2-(5-bromo-1H-indol-3-yl)vinyl)-6,7,10,11-tetrahydrodipyrido[2,1-a:1',2'-k][2,9]phenanthroline-5,12-diium trifluoromethanesulfonate, i.e. LSA-C9-30

(E)-13-(2-(dibenzo[b,d]furan-4-yl)vinyl)-4,5,8,9-tetrahydroisoquinolino[1,2-a]pyrido[1,2-k][2,9]phenanthroline-3,10-diium trifluoromethanesulfonate, i.e. MSB-C13-8

2,15-bis((E)-2-(2-methyl-1H-indol-3-yl)vinyl)-6,7,10,11-tetrahydrodipyrido[2,1-a:1',2'-k][2,9]phenanthroline-5,12-diium trifluoromethanesulfonate, i.e. PDA-C10-11

2,15-bis((E)-2-(1-methyl-1H-indol-3-yl)vinyl)-6,7,10,11-tetrahydrodipyrido[2,1-a:1',2'-k][2,9]phenanthroline-5,12-diium trifluoromethanesulfonate, i.e. PDA-C10-13

2,15-bis((E)-2-(2-phenyl-1H-indol-3-yl)vinyl)-6,7,10,11-tetrahydrodipyrido[2,1-a:1',2'-k][2,9]phenanthroline-5,12-diium trifluoromethanesulfonate, i.e. PDA-C15-8

2,15-bis((E)-2-(5-bromo-1H-indol-3-yl)vinyl)-6,7,10,11-tetrahydrodipyrido[2,1-a:1',2'-k][2,9]phenanthroline-5,12-diium trifluoromethanesulfonate, i.e. PDA-C9-30

(rac)-(E)-13-(2-(dibenzo[b,d]furan-4-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. MJA-C13-8

8,9-dimethyl-2,15-bis((E)-2-(2-methyl-1H-indol-3-yl)vinyl)-6,7,10,11-tetrahydrodipyrido[2,1-a:1',2'-k][2,9]phenanthroline-5,12-diium trifluoromethanesulfonate, i.e. PDB-C10-11

2,15-bis((E)-2-(1H-pyrrolo[2,3-b]pyridin-3-yl)vinyl)-8,9-dimethyl-6,7,10,11-tetrahydrodipyrido[2,1-a:1',2'-k][2,9]phenanthroline-5,12-diium trifluoromethanesulfonate, i.e. PDB-C8-14

2,4-bis((E)-2-(1H-indol-2-yl)vinyl)-6,7,10,11-tetrahydrodipyrido[2,1-a:1',2'-k][2,9]phenanthroline-5,12-diium trifluoromethanesulfonate, i.e. HTA-C10-10

2,4-bis((E)-2-([2,2'-bithiophen]-5-yl)vinyl)-6,7,10,11-tetrahydrodipyrido[2,1-a:1',2'-k][2,9]phenanthroline-5,12-diium trifluoromethanesulfonate, i.e. HTA-C9-16

2,4-bis((E)-2-(benzofuran-2-yl)vinyl)-6,7,10,11-tetrahydrodipyrido[2,1-a:1',2'-k][2,9]phenanthroline-5,12-diium trifluoromethanesulfonate, i.e. HTA-C9-17

(E)-2-(2-([2,2'-bithiophen]-5-yl)vinyl)-6,7,10,11-tetrahydrodipyrido[2,1-a:1',2'-k][2,9]phenanthroline-5,12-diium trifluoromethanesulfonate, i.e. LSA-C9-16

(E)-13-(2-(5-hexylthiophen-2-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. MJA-C11-25

(E)-13-(4-(9H-carbazol-9-yl)styryl)-6,7-dimethyl-4,5,8,9-tetrahydroisoquinolino[1,2-a]pyrido[1,2-k][2,9]phenanthroline-3,10-diium trifluoromethanesulfonate, i.e. MJA-C19-4

8,9-dimethyl-2,13-bis((E)-2-(4-methyl-1H-imidazol-5-yl)vinyl)-6,7,10,11-tetrahydrodipyrido[2,1-a:1',2'-k][2,9]phenanthroline-5,12-diium trifluoromethanesulfonate, i.e. MJB-C5-11

19-((E)-2-(3-methylbenzo[b]thiophen-2-yl)vinyl)-6,7,8,11,12,13-hexahydropyrido[1''',2''':1'',2'']azepino[4'',3'':5',6']

benzo[1',2':3,4]azepino[1,2-a]quinoline-5,14-diium trifluoromethanesulfonate, i.e. MSC-C10-36

19-((E)-2-([2,2'-bithiophen]-5-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, i.e. MSC-C9-16

19-((E)-2-(6-bromo-1H-indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, i.e. MSC-C9-18

2,15-bis((E)-2-(4-methyl-1H-imidazol-5-yl)vinyl)-6,7,10,11-tetrahydrodipyrido[2,1-a:1',2'-k][2,9]phenanthroline-5,12-diium trifluoromethanesulfonate, i.e. PDA-C5-11

2,15-bis((E)-2-(dibenzo[b,d]furan-4-yl)vinyl)-8,9-dimethyl-6,7,10,11-tetrahydrodipyrido[2,1-a:1',2'-k][2,9]phenanthroline-5,12-diium trifluoromethanesulfonate, i.e. PDB-C13-8

(rac)-2,4,13,15-tetrakis((E)-2-(thiophen-3-yl)vinyl)-6,7,8,11,12,13-hexahydro-dipyrido[1,2-a;1',2'-a']benzo[2,1-c:3,4-e]bisazepindiium trifluoromethanesulfonate, i.e. PRC-C5-9

(E)-13-(2-(dibenzo[b,d]furan-2-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. MJA-C13-22

(E)-13-(2-(4-phenylthiophen-2-yl)vinyl)-4,5,8,9-tetrahydroisoquinolino[1,2-a]pyrido[1,2-k][2,9]phenanthroline-3,10-diium trifluoromethanesulfonate, i.e. MSB-C11-7

(E)-13-(2-(1H-benzo[g]indol-3-yl)vinyl)-4,5,8,9-tetrahydroisoquinolino[1,2-a]pyrido[1,2-k][2,9]phenanthroline-3,10-diium trifluoromethanesulfonate, i.e. MSB-C13-16

19-((E)-2-(7-methyl-1H-indol-3-yl)vinyl)-6,7,8,11,12,13-hexahydropyrido[1',2''':1'',2'']azepino[4'',3'':5',6']benzo[1',2':3,4]azepino[1,2-a]quinoline-5,14-diium trifluoromethanesulfonate, i.e. MSC-C10-31

(E)-11-(2-(dibenzo[b,d]thiophen-4-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. VDJA-C13-20

(rac)-(E)-13-(2-(9-ethyl-9H-carbazol-3-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. MJA-C15-1

(rac)-8,9-dimethyl-2,13-bis((E)-2-(thiophen-3-yl)vinyl)-6,7,10,11-tetrahydrodipyrido[2,1-a: 1',2'-k][2,9]phenanthroline-5,12-diium trifluoromethanesulfonate, i.e. MJB-C5-9

(rac)-2,15-bis((E)-2-(1H-indol-3-yl)vinyl)-6,7,8,11,12,13-hexahydrodipyrido[1,2-a:1',2'-a']benzo[2,1-c:3,4-c']bisazepindiium trifluoromethanesulfonate, i.e. MJC-C9-7

4,13-bis((E)-2-(2-methyl-1H-indol-3-yl)vinyl)-6,7,10,11-tetrahydrodipyrido[2,1-a:1',2'-k][2,9]phenanthroline-5,12-diium trifluoromethanesulfonate, i.e. VDJC-C10-11

(E)-11-(2-(benzo[d]thiazol-2-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. VDJA-C8-5

(E)-6,7-dimethyl-11-(2-(5-phenylthiophen-2-yl)vinyl)-4,5,8,9-tetrahydroisoquinolino[1,2-a]pyrido[1,2-k][2,9]phenanthroline-3,10-diium trifluoromethanesulfonate, i.e. VDJA-C11-13

(rac)-(E)-2-(2-(4-nitro-1H-indol-3-yl)vinyl)-6,7,10,11-tetrahydropyrido[2,1-a:1',2'-k][2,9]phenanthroline-5,12-diium trifluoromethanesulfonate, i.e. LSA-C9-32

(rac)-(E)-2-(2-(6-isopropyl-1H-indol-3-yl)vinyl)-6,7,8,11,12,13-hexahydrodipyrido[1,2-a:1',2'-a']benzo[2,1-c:3,4-c']bisazepindiium trifluoromethanesulfonate, i.e. PSA-C12-6

(rac)-2,17-bis((E)-2-(1H-indol-5-yl)vinyl)-6,7,8,11,12,13-hexahydrodipyrido[1,2-a:1',2'-a']benzo[2,1-c:3,4-c']bisazepindiium trifluoromethanesulfonate, i.e. PRB-C9-10

(rac)-4,15-bis((E)-2-(2,5-dimethyl-1-(3-(trifluoromethyl)phenyl)-1H-pyrrol-3-yl)vinyl)-6,7,8,11,12,13-hexahydrodipyrido[1,2-a:1',2'-a']benzo[2,1-c:3,4-c']bisazepindiium trifluoromethanesulfonate, i.e. PRA-C14-6

8,9-dimethyl-2,15-bis((E)-2-(2-phenyl-1H-indol-3-yl)vinyl)-6,7,10,11-tetrahydrodipyrido[2,1-a:1',2'-k][2,9]phenanthroline-5,12-diium trifluoromethanesulfonate, i.e. PDB-C15-8

(rac)-2,4,15,17-tetrakis((E)-2-(1H-indol-2-yl)-6,7,8,11,12,13-hexahydro-dipyrido[1,2-a;1',2'-a']benzo[2,1-c:3,4-c']bisazepindiium trifluoromethanesulfonate, i.e. PRC-C9-11

(rac)-2,4-bis((E)-2-(1-methyl-1H-pyrrol-2-yl)vinyl)-6,7,10,11-tetrahydro-dipyrido[2,1-a:1',2'-k][2,9]phenanthroline-5,12-diium trifluoromethanesulfonate, i.e. HTA-C6-4

(rac)-2,4-bis((E)-2-(4-methyl-1H-imidazol-5-yl)vinyl)-6,7,10,11-tetrahydro-dipyrido[2,1-a:1',2'-k][2,9]phenanthroline-5,12-diium trifluoromethanesulfonate, i.e. HTA-C5-11

2,4,13,15-tetrakis((E)-2-(1-methyl-1H-indol-3-yl)vinyl)-6,7,10, 1-tetrahydrodipyrido[2,1-a:1',2'-k][2,9]phenanthroline-5,12-diium trifluoromethanesulfonate, i.e. TKA-C10-13.

Furthermore, object of the invention are helquat derivatives of general formula I of this invention and/or the above listed helquats or their pharmaceutically acceptable salts for use as medicaments.

Another object of the invention are helquat derivatives of general formula I of this invention and/or the above listed helquats or their pharmaceutically acceptable salts for use for stabilization of G-quadruplexes.

A further object of the invention are helquat derivatives of general formula I according to this invention and/or the above listed helquats or their pharmaceutically acceptable salts for use in the treatment of oncologic diseases.

Another object of the invention are helquat derivatives of general formula I according to this invention and/or the above listed helquats or their pharmaceutically acceptable salts for use as medicaments in the treatment of diseases related to increased cellular proliferation and in the treatment, requiring affecting G-quadruplex, preferably at telomeres or in gene promoters.

A further object of the invention is a pharmaceutical preparation, containing at least one helquat derivative of general formula I according to this invention and/or the above listed helquat or its pharmaceutically acceptable salt, and optionally also at least one pharmaceutically acceptable carrier, filler, or diluent and optionally another active ingredient.

A further object of the invention is the pharmaceutical preparation for use in the treatment of diseases related to increased cellular proliferation and in the treatment, requiring affecting of G-quadruplex, preferably at telomeres or in gene promoters.

Another object of the present invention is the use of helquat derivatives of general formula I according to this invention and/or the above listed helquats or their pharmaceutically acceptable salts for the manufacture of a medicament, in particular of a medicament for treatment of diseases, related to increased cellular proliferation, oncological diseases and in the treatment, requiring affecting of G-quadruplex, preferably at telomeres or in gene promoters.

Development of new G-quadruplex stabilizers remains an attractive and desirable field of research. Applied are especially original small molecules, efficient in repression of oncogene transcription, which at the same time have acceptable non-desired side effects. Ease of synthesis is an important issue for commercial preparation and use of novel G-quadruplex stabilizers. Advantage of the helquat derivatives presented in this invention is the fact that their isolation is possible without use of chromatography, which results in time and material savings.

The novel helquats surprisingly show a significantly improved effect in G-quadruplex stabilization. They thus represent a very promising new class of molecules, suitable for applications associated with G-quadruplex stabilization. They can be utilized to influence the protein expression, which is related with processes key to development and progression of cancer diseases such as proliferation, growth, invasiveness, metastasis, survival/resistance towards apoptosis, angiogenesis, et cetera. Among such proteins there are transcription factors c-myc, c-myb, HIF1α (hypoxia-inducible factor 1α), vascular endothelial growth factor (VEGF), platelet-derived growth factor α polypeptide (PDGFA), KRAS, protein BCL-2 (B cell lymphoma 2), PDGF receptor β polypeptide (PDGFRβ), protein subunit of human telomerase (TERT, human telomerase reverse transcriptase), ADAM-15.

Examples of diseases that can be treated by the compounds according to the invention include, but are not limited to: hematologic cancer (e.g. leukemia), lymphoma, myeloma, or solid cancers, for instance cancers of the breast, prostate, liver, bladder, lungs, oesophagus, stomach, further colorectal, urinary-sexual, gastrointestinal, skin, pancreatic cancers, cancers of brain, uterus, large intestine, head, throat, ovary, melanoma, astrocytoma, small-cell lung cancer, glioma, basal carcinomas and squamous cell carcinomas, sarcomas such as Kaposi's sarcoma and osteosarcoma, Further conditions that can be treated by the compounds according to the invention include, but are not limited to: disorders of T-cell formation such as aplastic anemia, DiGeorge syndrome, Graves-Basedow disease, Burkitt lymphoma, retinoblastoma, myeloid leukemia, medulloblastoma, B-cell chronic lymphocytic leukemia, maxillary sinus cancer, endocervical carcinoma, sinus cancer, bronchiolo-alveolar adenocarcinoma, uterine corpus cancer, diffuse large b-cell lymphoma, cerebral primitive neuroectodermal tumor, neuroectodermal tumor, childhood medulloblastoma, mature b-cell neoplasm, hereditary multiple exostoses, nodular malignant melanoma, plasma cell neoplasm, and hepatic angiomyolipoma.

The ability of the compounds of the invention to stabilize G-quadruplex was demonstrated using in vitro experiments: FRET analysis and ECD spectroscopy. Influencing the protein expression using the helquats of the present invention was demonstrated using dual luciferase reporter assay (DLR) analysis and Western Blot.

Measurement of an interaction of G-quadruplex with a ligand using FRET analysis is an established approach to assess the ability of a ligand to stabilize G-quadruplex. At the same time, this method enables to evaluate the selectivity of a ligand towards G-quadruplex as compared to double-stranded DNA [De Cian A. et al. (2007) *Methods*, 42, 183-195]. A series of helquats tested by this method proved their ability to significantly stabilize G-quadruplex, that is formed in an important part of regulatory sequence of c-myc gene promoter (tab. 1) and in human telomeres (tab. 2) even in presence of an excess of a competitor, represented by double-stranded DNA (ds26). It was found that helquats according to this invention stabilize G-quadruplex with a significantly greater selectivity as compared to an established G-quadruplex ligand TMPyP4, which is a frequently used positive control.

Measurement of ECD spectra is another sensitive method enabling determination of a G-quadruplex stabilization extent in presence of a ligand tested. ECD spectroscopy confirmed the ability of selected helquats (tab. 4) to significantly stabilize c-myc promoter G-quadruplex. This is evidenced by experiments using model oligonucleotide c-Myc27, which has the same oligonucleotide sequence as NHE III$_1$ segment in c-myc regulatory region.

Using dual luciferase analysis, unusually high ability of helquats to inhibit luciferase expression governed by regulatory region with NHE III$_1$ segment of c-myc gene was found. NHE III$_1$ region contains G-rich sequence capable of forming parallel G-quadruplex. It has been previously proven that stabilization of c-myc promoter G-quadruplex in NHE III segment leads to downregulation of expression of c-Myc transcription factor, or alternatively downregulation of expression of a reporter enzyme (firefly luciferase), expression of which is governed by this regulatory region [Siddiqui-Jain A. et al. (2002) *PNAS*, 99, 11593-11598; Brooks T. A. (2010), *Genes & Cancer*, 1, 641-649]. Analysis showed for example that five helquats (VDJA-C13-6, LSA-C13-8, MJA-C9-30, MJA-C13-8, MSC-C9-10) inhibited expression of firefly luciferase by more than 40% as compared to control (tab. 5). Specifically, in case of compound VDJA-C13-6 it was inhibition of expression by more than 70%. Nine helquats (VDJA-C13-8, MSC-C10-11, MSC-C9-30, MJB-C5-9, MJB-C5-3, LSA-C9-32, MJA-C8-28, MSC-C15-8, PDA-C8-27) inhibited expression by more than 20% and further five compounds (HTA-C5-9, MJB-C8-27, MSC-C13-16, MSC-C10-10, PRA-C12-5) by more than 10% as compared to control. The results were confirmed by minimum of two independent experiments (each in tetraplicate). In case of two compounds, MJA-C13-8 and VDJA-C13-6, concentration dependence of the given inhibition effect was proven (tab. 6). Details of the results are listed below in section entitled "Stabilization of G-quadruplex in promoter region of the c-myc gene".

On cellular level, using the immunodetection method, the short term effect of helquats (24 hours) on expression of c-myc protein was determined. Cancer cell line HGC-27 with higher expression levels of c-myc protein was used in these experiments. Helquats listed in table 7 led to at least 15% lower level of c-myc. In more than half of the compounds in the table 7 levels of c-myc were lowered by more than 40% as compared to control. Results were verified by minimum of two independent experiments. Thus, in significant number of helquats (MSC-C9-30, LSA-C13-8, MJA-C8-28, MJB-C5-9, MJA-C13-8, MSC-C15-8, PRC-C10-10, VDJA-C13-8) agreement was found between results obtained from dual luciferase analysis (influence of helquats on expression of a reporter enzyme governed by c-myc regulatory region) and results from c-myc protein quantification in cancer cells.

Antiproliferative effects of helquat treatments were tested over time of 72 hours using XTT cytotoxicity/proliferation test on cancer cell line CCRF-CEM and normal (non-cancer) cell line HUVEC from endothelial cells isolated from umbilical vein. Helquats listed in table 9 were markedly more toxic towards cancer cell line and non-toxic or less toxic towards non-cancer cell line. The ten helquats tested (MSC-C13-16, MSC-C9-30, MJA-C13-22, MSC-C9-16, MSC-C9-10, MSC-C10-10, MSB-C11-7, MSC-C10-11, VDJA-C13-20, LSA-C9-32) were toxic towards CCRF-CEM cells in concentrations lower than 25 $\mu mol \cdot l^{-1}$ and non-toxic towards HUVEC cells in concentrations higher than 100 $\mu mol \cdot l^{-1}$. The measured $IC_{50}$ values were obtained from at least three independent experiments.

The invention is hereinafter illustrated by the following examples, which should not be construed as further limiting.

EXAMPLES

Figure 1:
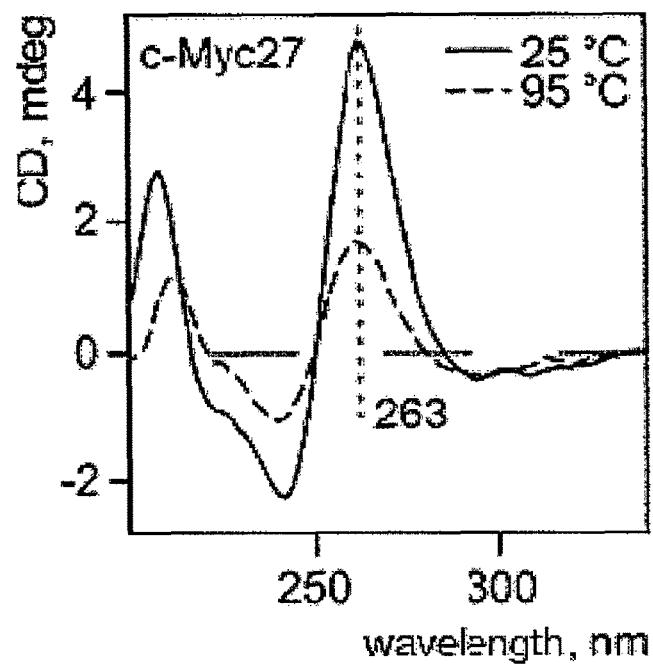
FIG. 1 represents the ECD spectra of c-Myc27 oligonucleotide at temperatures 25° C. and 95° C.; the vertical line corresponds to maximal difference in spectra signals and determines the wavelength selected for monitoring of G-quadruplex melting.

The numerical values of chemical shifts in NMR spectra are given in ppm. Notation used in the NMR spectra: s (singlet), d (doublet), t (triplet), q (quartet), m (multiples).
List of Abbreviations
ATCC/LGC American Type Cell Collection dle LGC standardů
BCA method method for quantification of protein amount based on use of 2,2'-biquinoline-4,4'-dicarboxylic acid
c-myc gene that codes transcription factor c-myc (avian myelocytomatosis virus oncogene cellular homolog)
c-myc transcription factor c-myc
DMSO dimethylsulfoxide
ds26 oligonucleotide forming double strand hairpin
ΔTm melting point difference
ECD electronic circular dichroism
EDTA disodium salt of ethylenediaminetetraacetic acid
EGF epidermal growth factor
F21T sequence from human telomere which has the length of 21 nucleotides, and is labelled at its end with FAM and at its 3'-end with TAMRA
FAM fluorescein
firefly luciferase luciferase derived from firefly luciferase
Fmyc27T sequence from promoter of c-myc gene 27 nucleotide long, able to form G-quadruplex, labelled at its 5'-end with FAM and at its 3'-end with TAMRA
FBS fetal bovine serum
FRET Förster resonance energy transfer
G guanine
c-Myc27 sequence from promoter of c-myc gene 27 nucleotide long, able to form G-quadruplex
h hour
HGC-27 human cell line derived from metastatic lymphatic node of a patient with stomach cancer
NHE III1 nuclease hypersensitive element (NHE) III1 found in promoter region of c-myc gene
HRP horseradish peroxidase
HSV-TK promoter of thymidin kinase of herpes simplex virus (HSV)
$IC_{50}$ concentration of a tested compound, which leads to decrease of viable cells to one half (ie. 50% decrease in cellular division) as compared to control non-treated cell population
PBS physiological solution buffered with phosphate buffer
PCR polymerase chain reaction
pGL4.10 (luc2) vector coding firefly luciferase without promoter
pGL4.10-myc (luc2) vector coding firefly luciferase with regulatory part c-myc
PhIC mixture of phosphatase inhibitors
PMS phenazine methosulfate
PrIC mixture of protease inhibitors
pRL-TK mammalian co-reporter vector with low constitutive expression of Renilla luciferase
PVDF membrane polyvinylidene difluoride membrane
RIPA radioimmunoprecipitation assay buffer
SD standard deviation
SDS-PAGE polyacrylamide gel with sodium dodecylsulphate for electrophoresis
TAMRA carboxytetramethylrhodamine
TBS-T solution of tris(hydroxymethyl)aminomethane, sodium chloride and Tween-20 (50 $mmol \cdot l^{-1}$ Tris, 150 $mmol \cdot l^{-1}$ NaCl, 0.05% Tween-20)
I. Synthesis of Compounds
Structures A to Q of starting helquats are as follows:

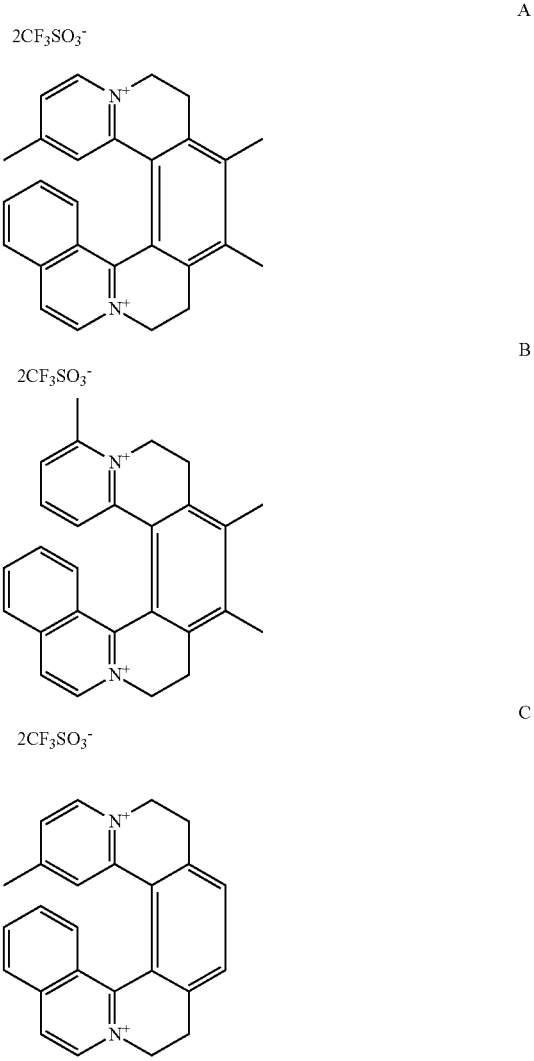

-continued
2CF$_3$SO$_3^-$
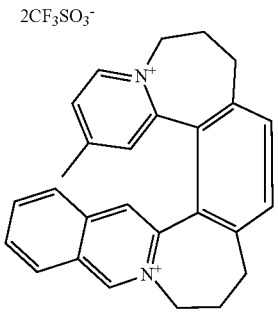
D
2CF$_3$SO$_3^-$
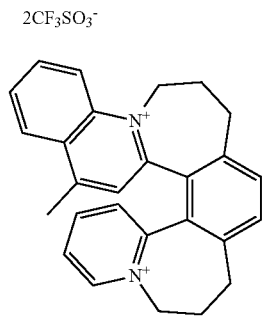
I
2CF$_3$SO$_3^-$
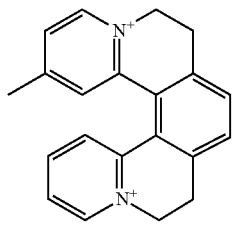
E
2CF$_3$SO$_3^-$
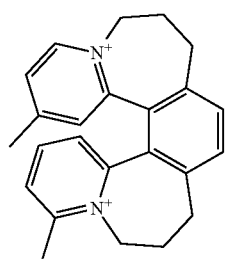
J
2CF$_3$SO$_3^-$
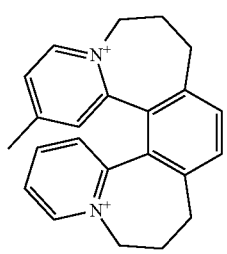
F
2CF$_3$SO$_3^-$
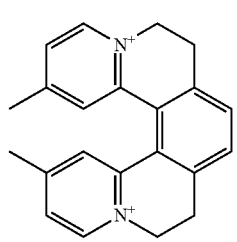
K
2CF$_3$SO$_3^-$
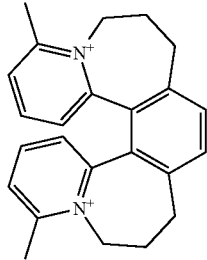
G
2CF$_3$SO$_3^-$
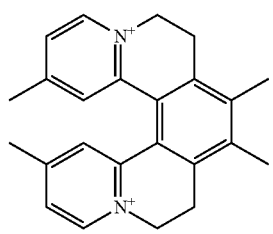
L
2CF$_3$SO$_3^-$
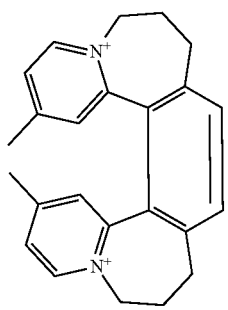
H
2CF$_3$SO$_3^-$
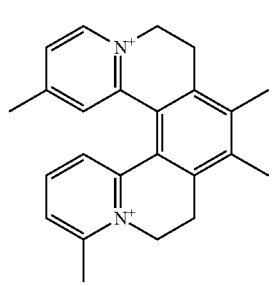
M -continued

N

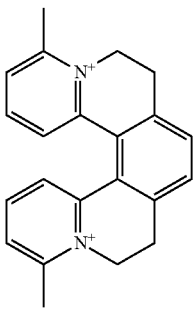
2CF₃SO₃⁻

O

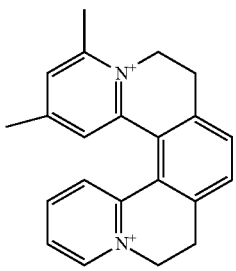
2CF₃SO₃⁻

P

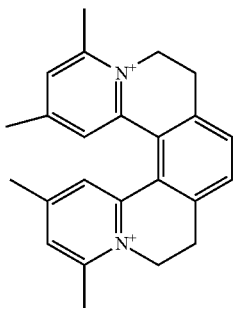
2CF₃SO₃⁻

Q

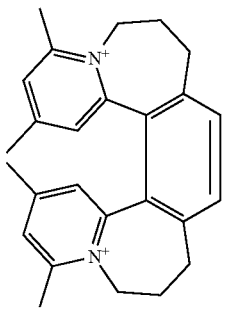
2CF₃SO₃⁻

Example 1

(rac)-(E)-13-(2-(dibenzo[b,d]furan-4-yl)vinyl)-6,7-dimethyl-4,5,8,9-tetrahydroisoquinolino[1,2-a]pyrido[1,2-k][2,9]phenanthroline-3,10-diium trifluoromethanesulfonate, MJA-C13-8

Starting helquat A (40 mg, 1 equiv, 59 μmol), dibenzo[b,d]furan-4-carbaldehyde (60 mg, 5 equiv, 306 μmol), pyrrolidine (30 mg, 35 μl, 7 equiv, 419 μmol) and dry methanol (1 ml) were placed into a 5 ml flask and the resulting mixture was stirred under argon for 2 h at room temperature. Progress of the reaction was monitored by thin layer chromatography. The crude product was precipitated from the reaction mixture by addition of diethylether (40 ml). The suspension was centrifuged and the liquid was separated from the solid pellet. The solids were partially dissolved in methanol (3 ml), the resulting mixture was mixed and the solubilized product was precipitated by addition of diethylether (40 ml). Then, this suspension was centrifuged, the liquid part was removed and this cleaning procedure was repeated two more times for the solid part. The solid part was then dried under vacuum of an oil pump to get 36 mg (42 μmol, 71% yield) of a light-yellow solid as a pure product. MJA-C13-8.

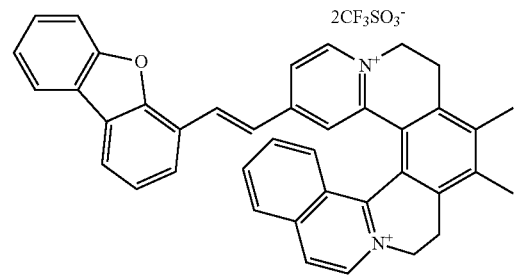 [SMILES: Cc1c(C)c2c(c3c1CC[n+]1ccc(/C=C/c4cccc5c4oc4ccccc45)cc1-3)-c1c3ccccc3cc[n+]1CC2]
2CF₃SO₃⁻

¹H NMR (400 MHz, acetone-d₆): 2.67 (s, 3H), 2.67 (s, 3H), 3.31 (m, 2H), 3.69 (dq, J=5.4, 1.9 Hz, 1H), 3.73 (ddd, J=7.5, 3.4, 1.7 Hz, 1H), 5.04 (m, 3H), 5.21 (ddd, J=13.9, 4.5, 1.6 Hz, 1H), 7.16 (d, J=1.8 Hz, 1H), 7.35 (d, J=16.4 Hz, 1H), 7.43 (d, J=16.4 Hz, 1H), 7.57 (t, J=7.6 Hz, 1H), 7.60 (td, J=7.7, 0.9 Hz, 1H), 7.69 (dd, J=7.7, 0.8 Hz, 1H), 7.76 (ddd, J=9.7, 6.7, 1.3 Hz, 2H), 7.82 (dd, J=6.6, 1.9 Hz, 1H), 8.15 (d, J=8.0 Hz, 1H), 8.24 (dd, J=7.7, 0.5 Hz, 1H), 8.25 (dd, J=7.6, 1.2 Hz, 1H), 8.49 (d, J=6.7 Hz, 1H), 8.68 (d, J=6.6 Hz, 1H), 8.90 (d, J=6.7 Hz, 1H).

Example 2

(rac)-(E)-13-(2-(9-ethyl-9H-carbazol-3-yl)vinyl)-6,7-dimethyl-4,5,8,9-tetrahydroisoquinolino[1,2-a]pyrido[1,2-k][2,9]phenanthroline-3,10-diium trifluoromethanesulfonate, MJA-C15-1

Starting helquat A (100 mg, 1 equiv, 148 μmol), 9-ethyl-9H-carbazole-3-carbaldehyde (66 mg, 2 equiv, 296 μmol), pyrrolidine (74 mg, 86 μl, 7 equiv, 1.035 mmol) and dry methanol (1 ml) were placed into a 5 ml flask and the resulting mixture was stirred under argon for 2 h at room temperature. Progress of the reaction was monitored by thin layer chromatography. The crude product was precipitated from the reaction mixture by addition of diethylether (40 ml). The suspension was centrifuged and the liquid was separated from the solid pellet. The solids were partially dissolved in methanol (5 ml), the resulting mixture was mixed and the solubilized product was precipitated by addition of diethylether (40 ml). Then, this suspension was centrifuged, the liquid part was removed and this cleaning procedure was repeated two more times for the solid part. The solid part was then dried under vacuum of an oil pump to get 67 mg (76 μmol, 51% yield) of a light-yellow solid as a pure product. MJA-C15-1.

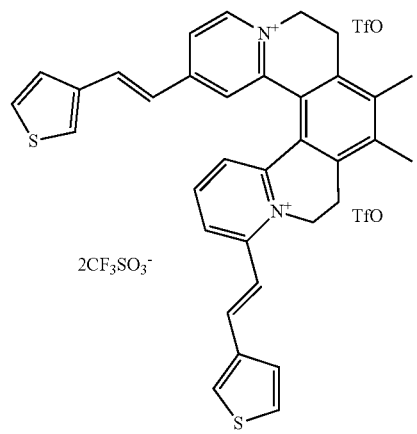

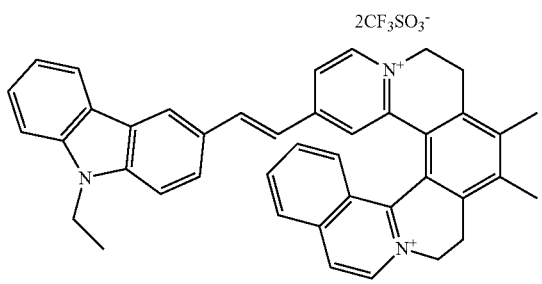 [SMILES: CCn1c2ccccc2c2cc(/C=C/c3cc[n+]4c(c3)-c3c(c(C)c(C)c5c3-c3c6ccccc6cc[n+]3CC5)CC4)ccc21]

$^1$H NMR (400 MHz, acetone-d$_6$) δ 1.45 (t, J=7.2 Hz, 3H), 2.12 (s, 3H), 2.32 (s, 3H), 3.11 (td, J=16.0, 4.5 Hz, 1H), 3.26 (m, 2H), 3.58 (dd, J=15.3, 1.6 Hz, 1H), 4.58 (q, J=7.2 Hz, 2H), 5.00 (td, J=14.1, 3.6 Hz, 1H), 5.13 (dd, J=13.8, 3.7 Hz, 1H), 5.29 (m, 2H), 6.77 (d, J=16.2 Hz, 1H), 7.31 (d, J=1.5 Hz, 1H), 7.35 (t, J=7.4 Hz, 1H), 7.43 (d, J=16.2 Hz, 1H), 7.60 (m, 4H), 7.69 (t, J=8.2 Hz, 1H), 7.78 (dd, J=6.7, 1.8 Hz, 1H), 7.82 (t, J=7.2 Hz, 1H), 7.90 (d, J=8.7 Hz, 1H), 8.03 (d, J=8.1 Hz, 1H), 8.27 (d, J=7.7 Hz, 1H), 8.40 (s, 1H), 8.41 (d, J=6.6 Hz, 1H), 8.74 (d, J=6.6 Hz, 1H), 8.97 (d, J=6.7 Hz, 1H).

Example 3

(rac)-8,9-dimethyl-2,13-bis((E)-2-(thiophen-3-yl)vinyl)-6,7,10,11-tetrahydrodipyrido[2,1-a:1',2'-k][2,9]phenanthroline-5,12-diium trifluoromethanesulfonate, MJB-C5-9

Starting helquat M (40 mg, 1 equiv, 62 μmol), thiophene-3-carbaldehyde (210 mg, 30 equiv, 1.873 mmol), pyrrolidine (67 mg, 78 μl, 15 equiv, 937 μmol) and dry methanol (1 ml) were placed into a 5 ml flask and the resulting mixture was stirred under argon for 12 h at room temperature. Progress of the reaction was monitored by thin layer chromatography. The crude product was precipitated from the reaction mixture by addition of diethylether (40 ml). The suspension was centrifuged and the liquid was separated from the solid pellet. The solids were partially dissolved in methanol (5 ml), the resulting mixture was mixed and the solubilized product was precipitated by addition of diethylether (40 ml). Then, this suspension was centrifuged, the liquid part was removed and this cleaning procedure was repeated two more times for the solid part. The solid part was then dried under vacuum of an oil pump to get 48 mg (43 μmol, 69% yield) of a light-yellow solid as a pure product. MJB-C5-9.

$^1$H NMR (400 MHz, acetonitrile-d$_3$) δ 2.44 (s, 3H), 2.44 (s, 3H), 3.03 (m, 2H), 3.45 (m, 2H), 4.53 (td, J=14.6, 3.4 Hz, 1H), 4.61 (td, J=15.6, 15.2, 3.7 Hz, 1H), 4.83 (dd, J=14.0, 4.0 Hz, 1H), 5.30 (dd, J=14.2, 3.3 Hz, 1H), 6.96 (d, J=16.3 Hz, 1H), 7.38 (dd, J=5.1, 1.0 Hz, 1H), 7.46 (dd, J=5.1, 2.9 Hz, 1H), 7.50 (d, J=15.9 Hz, 1H), 7.53 (d, J=16.2 Hz, 1H), 7.60 (dd, J=5.4, 3.2 Hz, 1H), 7.62 (d, J=2.1 Hz, 1H), 7.66 (d, J=1.9 Hz, 1H), 7.69 (d, J=6.4 Hz, 2H), 7.73 (d, J=15.9 Hz, 1H), 7.88 (dd, J=7.3, 2.5 Hz, 1H), 7.89 (dd, 2.9, 1.0 Hz, 1H), 8.00 (t, J=8.0 Hz, 1H), 8.06 (dd, J=8.2, 1.4 Hz, 1H), 8.56 (d, J=6.6 Hz, 1H).

Example 4

(rac)-2,15-bis(E)-2-(1H-indol-3-yl)vinyl)-6,7,8,11,12,13-hexahydrodipyrido[1,2-a:1',2'-a']benzo[2,1-c:3,4-c']bisazepindiium trifluoromethanesulfonate, MJC-C9-7

Starting helquat J (35 mg, 1 equiv, 55 μmol), 1H-indole-3-carbaldehyde (238 mg, 30 equiv, 1.639 mmol), pyrrolidine (58 mg, 68 μl, 15 equiv, 820 μmol) and dry methanol (1 ml) were placed into a 5 ml flask and the resulting mixture was stirred under argon for 16 h at room temperature. Progress of the reaction was monitored by thin layer chromatography. The crude product was precipitated from the reaction mixture by addition of diethylether (40 ml). The suspension was centrifuged and the liquid was separated from the solid pellet. Diethylether (35 ml) was added to the solid, the suspension was stirred and centrifuged. The resulting solid part was partially dissolved in methanol (3 ml), the mixture was stirred and the solubilized product was precipitated by addition of diethylether (40 ml). Then, this suspension was centrifuged, the liquid part was removed and this cleaning procedure was repeated two more times for the solid part. The solid part was then dried under vacuum of an oil pump to get 32 mg (36 μmol, 66% yield) of a red solid as a pure product. MJC-C9-7.

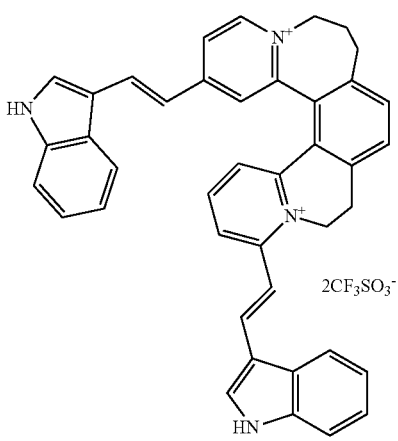 [SMILES: C(=C\c1c[nH]c2ccccc12)/c1cc[n+]2c(c1)-c1c(ccc3c1-c1cccc(/C=C/c4c[nH]c5ccccc45)[n+]1CC3)CCC2]

¹H NMR (400 MHz, acetonitrile-d₃) δ 2.34 (m, 2H), 2.49 (m, 2H), 2.61 (m, 1H), 2.80 (m, 1H), 2.99 (dd, J=14.1, 6.5 Hz, 1H), 3.07 (m, 1H), 4.35 (td, J=13.4, 5.0 Hz, 1H), 4.40 (dd, J=15.6, 5.3 Hz, 1H), 4.58 (dd, J=13.9, 6.3 Hz, 1H), 5.13 (dd, J=14.6, 5.5 Hz, 1H), 6.98 (dd, J=7.7, 1.1 Hz, 1H), 7.03 (d, J=16.2 Hz, 1H), 7.12 (d, J=1.9 Hz, 1H), 7.15 (d, J=8.0 Hz, 1H), 7.22 (t, J=7.6 Hz, 1H), 7.30-7.38 (m, 3H), 7.50 (d, J=8.1 Hz, 1H), 7.59 (dd, J=6.0, 2.8 Hz, 1H), 7.68 (d, J=7.8 Hz, 1H), 7.70 (d, J=7.8 Hz, 1H), 7.73 (s, 1H), 7.88-8.01 (m, 5H), 8.02-8.06 (m, 1H), 8.09 (d, J=15.6 Hz, 1H), 8.20 (d, J=8.5 Hz, 1H), 8.51 (d, J=6.8 Hz, 1H).

Example 5

4,13-bis((E)-2-(2-methyl-1H-indol-3-yl)vinyl)-6,7,10,11-tetrahydrodipyrido[2,1-a:1',2'-k][2,9]phenanthroline-5,12-diium trifluoromethanesulfonate, VDJC-C10-11

Starting racemic helquat N (10 mg, 16.3 μmol), 2-methyl-1H-indole-3-carbaldehyde (78 mg, 489.7 μmol), pyrrolidine (20 μl, 244.8 μmol) and dry methanol (1 ml) were placed into a 10 ml flask and the resulting mixture was stirred under argon for 24 h at room temperature. Progress of the reaction was monitored by thin layer chromatography. The crude product was precipitated from the reaction mixture by addition of diethylether (8 ml). The resulting suspension was centrifuged and the supernatant was separated from the solid pellet. The solids were dissolved in acetonitrile (6 ml) and the pure product was precipitated by addition of diethylether (36 ml). Then, centrifugation of this suspension, removal of the supernatant and drying of the solid part under vacuum of an oil pump led to 8.7 mg (9.8 μmol, 60% yield) of an orange solid VDJC-C10-11.

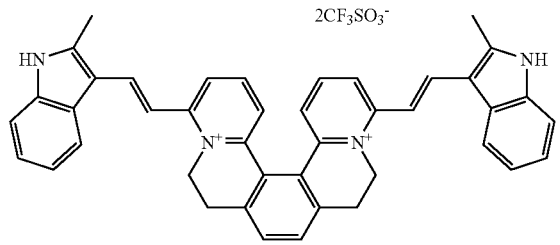 [SMILES: Cc1[nH]c2ccccc2c1/C=C/c1cccc2[n+]1CCc1ccc3c(c1-2)-c1cccc(/C=C/c2c(C)[nH]c4ccccc24)[n+]1CC3]

¹H NMR (400 MHz, acetonitrile-d₃): 2.68 (s, 6H), 3.08-3.23 (m, 4H), 4.31-4.58 (m, 2H), 5.16-5.36 (m, 2H), 7.27-7.33 (m, 6H), 7.48 (dd, J=2.1, 5.6 Hz, 2H), 7.50 (dd, J=1.3, 7.9 Hz 2H), 7.69 (s, 2H), 7.91 (t, J=8.1 Hz, 2H), 7.99 (d, J=15.5 Hz, 2H), 8.06 (dd, J=2.0, 5.4 Hz, 2H), 8.21 (dd, J=1.1, 8.4 Hz, 2H), 10.15 (bs, 2H).

Example 6

(E)-11-(2-(benzo[d]thiazol-2-yl)vinyl)-6,7-dimethyl-4,5,8,9-tetrahydroisoquinolino[1,2-a]pyrido[1,2-k][2,9]phenanthroline-3,10-diium trifluoromethanesulfonate, VDJA-C8-5

Starting racemic helquat B (20 mg, 29.6 μmol), benzo[d]thiazole-2-carbaldehyde (121 mg, 739 μmol), pyrrolidine (30 μl, 367.2 μmol) and dry acetonitrile (2 ml) were placed into a 10 ml flask and the resulting mixture was stirred under argon for 1 h at room temperature. Progress of the reaction was monitored by thin layer chromatography. The crude product was precipitated from the reaction mixture by addition of diethylether (16 ml). The suspension was centrifuged and the supernatant was separated from the solid pellet. The solids were dissolved in methanol (2 ml) and the pure product was precipitated by addition of diethylether (12 ml). Then, centrifugation of this suspension, removal of the supernatant and drying of the solid part under vacuum of an oil pump led to 14 mg (17.0 μmol, 58% yield) of an orange solid VDJA-C8-5.

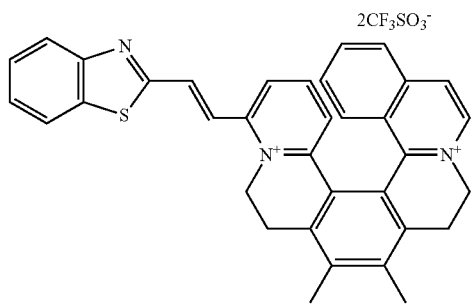 [SMILES: Cc1c(C)c2c(c3c1CC[n+]1ccc4ccccc4c1-3)-c1cccc(/C=C/c3nc4ccccc4s3)[n+]1CC2]

¹H NMR (400 MHz, acetone-d₆): 2.67 (s, 3H), 2.68 (s, 3H), 3.49-3.54 (m, 2H), 3.82 (dq, J=1.7, 17.1 Hz, 1H), 3.89 (dq, J=1.7, 17.1 Hz, 1H), 5.17 (dt, J=3.4, 14.6 Hz, 1H), 5.33 (dt, J=3.7, 14.0 Hz, 1H), 5.40 (dd, J=1.6, 13.9 Hz, 1H), 5.75 (dd, J=1.6, 13.9 Hz, 1H), 7.61 (dt, J=1.2, 7.2 Hz, 1H), 7.64 (dt, J=1.3, 8.2 Hz, 1H), 7.69 (dt, J=1.3, 7.2 Hz, 1H), 7.88 (dt, J=1.2, 6.8 Hz, 1H), 7.91 (t, J=8.1 Hz, 1H), 8.00 (d, J=15.8 Hz, 1H), 8.02 (t, J=1.2 Hz, 1H), 8.17 (dq, J=0.7, 8.1 Hz, 1H), 8.18 (dd, J=0.8, 8.7 Hz, 1H), 8.22 (dq, J=0.7, 8.1 Hz, 1H), 8.24 (dd, J=1.3, 8.1 Hz, 1H), 8.31 (d, J=9.2 Hz, 1H), 8.41 (d, J=15.9 Hz, 1H), 8.58 (d, J=6.7 Hz, 1H), 9.06 (d, J=6.7 Hz, 1H).

Example 7

(E)-6,7-dimethyl-11-(2-(5-phenylthiophen-2-yl)vinyl)-4,5,8,9-tetrahydroisoquinolino[1,2-a]pyrido[1,2-k][2,9]phenanthroline-3,10-diium trifluoromethanesulfonate, VDJA-C11-13

Starting racemic helquat B (10 mg, 14.78 μmol), 5-phenylthiophene-2-carbaldehyde (53.87 mg, 147.8 μmol), pyrrolidine (15 μl, 183.6 μmol), and dry methanol (1 ml) were placed into a 10 ml flask and the resulting mixture was stirred under argon for 2 h at room temperature. Progress of the reaction was monitored by thin layer chromatography. The crude product was precipitated from the reaction mixture by addition of diethylether (8 ml). The suspension was centrifuged and the supernatant was separated from the solid pellet. The solids were dissolved in methanol (2 ml) and the pure product was precipitated by addition of diethylether (16 ml). Then, centrifugation of this suspension, removal of the supernatant and drying of the solid part under vacuum of an oil pump led to 9.0 mg (10.6 μmol, 72% yield) of a yellow solid VDJA-C11-13.

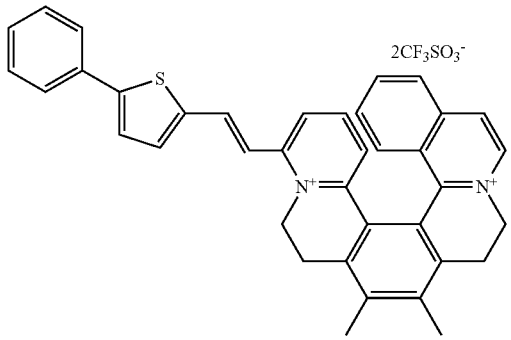 [SMILES: Cc1c(C)c2c(c3c1CC[n+]1ccc4ccccc4c1-3)-c1cccc(/C=C/c3ccc(-c4ccccc4)s3)[n+]1CC2]

¹H NMR (400 MHz, acetone-d₆): 2.64 (s, 3H), 2.65 (s, 3H), 3.11-3.31 (m, 2H), 3.62 (dd, J=2.0, 17.2 Hz, 1H), 3.66 (dd, J=1.7, 17.4 Hz, 1H), 4.80 (dt, J=2.6, 13.0 Hz, 1H), 4.89 (dt, J=2.6, 13.0 Hz, 1H), 5.10 (dd, J=2.1, 13.9 Hz, 1H), 5.39 (dd, J=2.1, 13.9 Hz, 1H), 6.95 (dd, J=1.1, 6.8 Hz, 1H), 7.44 (d, J=15.7 Hz, 1H), 7.54 (dt, J=7.3, 1.4, 2.16 Hz, 1H), 7.59 (dd, J=1.5, 2.2 Hz, 1H), 7.61 (d, J=3.9, 1H), 7.63 (d, J=3.9 Hz, 1H), 7.64 (d, J=3.9 Hz, 1H), 7.66 (d, J=3.9 Hz, 1H), 7.76 (dd, J=1.2, 7.3 Hz, 1H), 7.86-7.91 (m, 5H), 7.99 (dd, J=1.1, 7.1 Hz, 1H), 8.22 (d, J=9.3 Hz, 1H), 8.40 (d, J=6.7 Hz, 1H), 8.70 (d, J=6.8 Hz, 1H).

Example 8

(rac)-(E)-2-(2-(4-nitro-1H-indol-3-yl)vinyl)-6,7,10,11-tetrahydrodipyrido[2,1-a:1',2'-k][2,9]phenanthroline-5,12-diium trifluoromethanesulfonate, LSA-C9-32

Starting racemic helquat E (12.7 mg, 21.2 µmol, 1 equiv), 4-nitro-1H-indole-3-carbaldehyde (52.3 mg, 275.0 µmol, 13 equiv), piperidine (25 µl, 21.7 mg, 254.6 µmol, 12 equiv) and dry methanol (1 ml) were placed into a Schlenk tube and the resulting mixture was stirred under argon for 6 h at room temperature. Progress of the reaction was monitored by thin layer chromatography. The crude product was precipitated from the reaction mixture by addition of diethylether (15 ml). The suspension was centrifuged and the supernatant was separated from the solid pellet. The solids were dissolved in methanol (1 ml) and the pure product was precipitated by addition of diethylether (15 ml) two times. Then, centrifugation of this suspension, removal of the supernatant and drying of the solid part under vacuum of an oil pump led to 13.1 mg (17.0 µmol, 80% yield) of a dark solid.

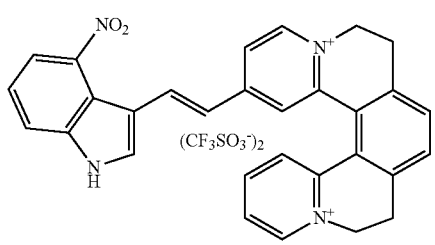

¹H NMR (400 MHz, acetonitrile-d₃-1.94): 3.25-3.33 (m, 4H), 4.60-4.98 (m, 4H), 6.82 (d, J=16.0, 11-1), 7.32 (t, J=8.0; 8.0 Hz, 1H), 7.68-7.70 (m, 4H), 7.87-7.91 (m, 2H), 7.96 (dd, J=8.0; 1.0 Hz, 1H), 7.98 (dd, J=15.9; 0.7 Hz, 1H), 8.06 (dd, J=8.3; 1.5 Hz, 1H), 8.11 (s, 1H), 8.20 (td, J=7.9; 7.9; 1.5 Hz, 1H), 8.45 (d, J=7.3 Hz, 1H), 8.86 (dd, J=6.4; 1.3 Hz, 1H).

Example 9

(rac)-(E)-2-(2-(6-isopropyl-1H-indol-3-yl)vinyl)-6,7,8,11,12,13-hexahydrodipyrido[1,2-a:1',2'-a']benzo[2,1-c:3,4-c']bisazepindiium trifluoromethanesulfonate, PSA-C12-6

Starting racemic helquat F (14.2 mg, 22.7 µmol, 1 equiv), 6-isopropyl-1H-indole-3-carbaldehyde (63.2 mg, 337.5 nmol, 15 equiv), pyrrolidine (15 µl, 12.9 mg, 181.3 µmol, 8 equiv) and dry methanol (1 ml) were placed into a Schlenk tube and the resulting mixture was stirred under argon for 1.5 h at room temperature. Progress of the reaction was monitored by thin layer chromatography. The crude product was precipitated from the reaction mixture by addition of diethylether (15 ml). The suspension was centrifuged and the supernatant was separated from the solid pellet. The solids were dissolved in acetonitrile (1 ml) and the pure product was precipitated by addition of diethylether (15 ml) two times. Then, centrifugation of this suspension, removal of the supernatant and drying of the solid part under vacuum of an oil pump led to 13.7 mg (17.2 µmol, 76% yield) of a brown solid. PSA-C12-6.

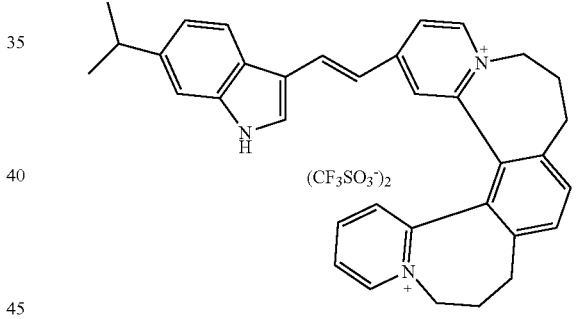

¹H NMR (400 MHz, acetonitrile-d₃-1.94): 1.28 (d, J=6.9 Hz, 6H), 2.26-2.72 (m), 2.96-3.06 (m), 4.28-4.36 (m, 1H), 4.53 (dd, J=14.0; 6.1 Hz, 1H), 4.63 (td, J=13.4; 13.2; 5.6 Hz, 1H), 4.86 (dd, J=13.6; 6.3 Hz, 1H), 6.90 (d, J=16.0, 1H), 6.93 (d, J=2.2 Hz, 1H), 7.16 (dd, J=8.3; 1.6 Hz, 1H), 7.39-7.41 (m, 2H), 7.69 (s, 2H), 7.71 (s, 1H), 7.83-7.90 (m, 3H), 7.93 (ddd, J=7.8; 6.2; 1.5 Hz, 1H), 8.23 (td, J=7.9; 7.9; 1.5 Hz, 1H), 8.45 (d, J=6.9 Hz, 1H), 8.91 (dd, J=6.2; 1.8 Hz, 1H).

Example 10

(rac)-2,17-bis((E)-2-(1H-indol-5-yl)vinyl)-6,7,8,11,12,13-hexahydrodipyrido[1,2-a:1',2'-a']benzo[2,1-c:3,4-c']bisazepindiium trifluoromethanesulfonate PRB-C9-10

Starting racemic helquat H (30 mg, 47 mol, 1 equiv), 1H-indole-5-carbaldehyde (204 mg, 1.40 mmol, 30 equiv), piperidine (74 µl, 750 µmol) and dry methanol (1 ml) were placed into a 10 ml flask and the resulting mixture was stirred under argon for 1 h at room temperature. Progress of the reaction was monitored by thin layer chromatography. The crude product was precipitated from the reaction mixture by addition of diethylether (34 ml). The suspension was centrifuged and the supernatant was separated from the solid pellet. The solids were dissolved in methanol (2 ml) and the pure product was precipitated by addition of diethylether (34 ml) four times. Then, centrifugation of this suspension, removal of the supernatant and drying of the solid part under vacuum of an oil pump led to 24 mg (27 μmol, 57% yield) of an orange solid PRB-C9-10.

pure product was precipitated by addition of diethylether (34 ml) four times. To the solid pellet was added THF (0.5 ml) and the suspension was centrifuged. After removal of the supernatant, the solid part was cleaned two times by diethylether (5 ml). Then, centrifugation of this suspension, removal of the supernatant and drying of the solid part under vacuum of an oil pump led to 34 mg (30 μmol, 64% yield) of a yellow solid PRA-C14-6.

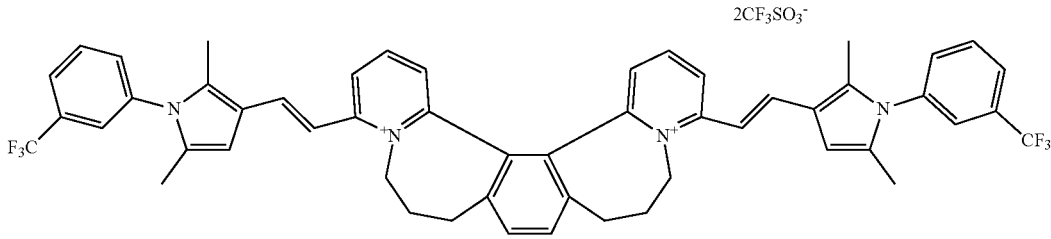

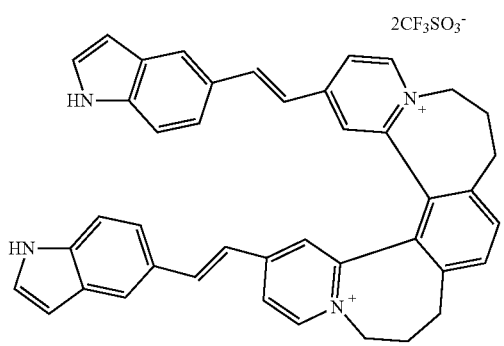

$^1$H NMR (400 MHz, acetonitrile-d$_3$): 2.34-2.44 (m, 1H), 2.46-2.67 (m, 1H), 2.60-2.69 (m, 1H), 3.01 (dd, J=6.2, 13.7 Hz, 1H), 4.46 (td, J=5.6, 13.2 Hz, 1H), 4.71 (dd, J=6.2, 13.8 Hz, 1H), 6.53-6.54 (m, 1H), 7.09 (d, J=16.2 Hz, 1H), 7.14 (d, J=1.8 Hz, 1H), 7.31-7.32 (m, 1H), 7.43-7.50 (m, 2H), 7.70 (s, 1H), 7.72 (d, J=16.1 Hz, 1H), 7.83 (s, 1H), 7.99 (dd, J=1.9, 6.7 Hz, 1H), 8.66 (d, J=6.7 Hz, 1H), 9.63 (bs, 1H).

$^1$H NMR (400 MHz, acetonitrile-d$_3$): 2.04 (s, 3H), 2.20 (s, 3H), 2.29-2.38 (m, 1H), 2.41-2.49 (m, 1H), 2.70 (tt, J=5.9, 13.0 Hz, 1H), 3.03 (dd, J=5.9, 13.8 Hz, 1H), 4.28 (td, J=5.0, 14.1 Hz, 1H), 4.99 (dd, J=5.6, 14.5 Hz, 1H), 6.62 (s, 1H), 6.93 (dd, J=1.3, 7.7 Hz, 1H), 6.99 (d, J=15.1 Hz, 1H), 7.57-7.60 (m, 1H), 7.67-7.68 (m, 2H), 7.78 (t, J=7.9 Hz, 1H), 7.84-7.91 (m, 3H), 8.24 (dd, J=1.0, 8.6 Hz, 1H).

Example 12

2,15-bis((E)-2-(2,6-dimethoxypyridin-3-yl)vinyl)-6,7,10,11-tetrahydrodipyrido[2,1-a:1',2'-k][2,9]phenanthroline-5,12-diium trifluoromethanesulfonate, PDA-C8-27

Starting racemic helquat K (30 mg, 49.0 μmol), 2,6-dimethoxynicotinaldehyde (245.6 mg, 1.47 mmol), piperidine (72 μl, 734.6 μmol) and dry methanol (2 ml) were placed into a 10 ml flask and the resulting mixture was stirred under argon for 6 h at room temperature. Progress of the reaction was monitored by thin layer chromatography. The crude product was precipitated from the reaction mixture by addition of diethylether (30 ml). The suspension was centrifuged and the supernatant was separated from the solid pellet. The solids were dissolved in methanol (1 ml) and the pure product was precipitated by addition of diethylether (30 ml). Then, centrifugation of this suspension, removal of the supernatant and drying of the solid part under vacuum of an oil pump led to 35 mg (38.4 μl, 78% yield) of a yellow solid PDA-C8-27.

Example 11

(rac)-4,15-bis((E)-2-(2,5-dimethyl-1-(3-(trifluoromethyl)phenyl)-1H-pyrrol-3-yl)vinyl)-6,7,8,11,12,13-hexahydrodipyrido[1,2-a:1',2'-a']benzo[2,1-c:3,4-c']bisazepindiium trifluoromethanesulfonate, PRA-C14-6

Starting racemic helquat G (30 mg, 47 μmol, 1 equiv), 2,5-dimethyl-1-(3-(trifluoromethyl)phenyl)-1H-pyrrole-3-carbaldehyde (375 mg, 1.40 mmol, 30 equiv), pyrrolidine (62.5 μl, 750 μmol) and dry methanol (1 ml) were placed into a 10 ml flask and the resulting mixture was stirred under argon for 30 min at room temperature. Progress of the reaction was monitored by thin layer chromatography. The crude product was precipitated from the reaction mixture by addition of diethylether (34 ml). The suspension was centrifuged and the supernatant was separated from the solid pellet. The solids were dissolved in methanol (2 ml) and the

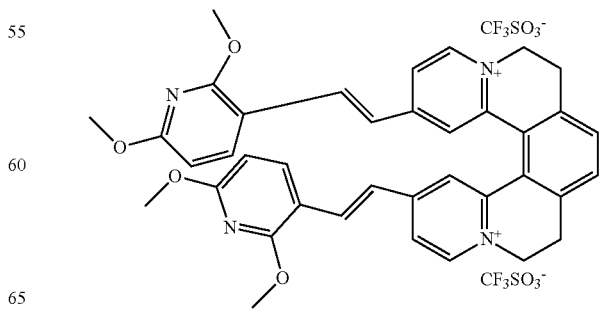

¹H NMR (400 MHz, acetonitrile-d₃): 3.26-3.30 (m, 4H), 3.94 (s, 6H), 3.99 (s, 6H), 4.68-4.72 (m, 2H), 438-4.81 (m, 2H), 6.37 (d, J=8.32 Hz, 214), 7.04 (d, J=16.32 Hz, 2H), 737 (d, J=16.32 Hz, 2H), 7.68-7.71 (m, 4H), 7.85 (dd, J₁=1.93 Hz, J₂=6.64 Hz, 2H), 7.98 (d, J=1.85 Hz, 2H), 8.60 (d, J=6.64 Hz, 2H)

Example 13

2,15-bis((E)-2-(1-methyl-1H-indol-3-yl)vinyl)-6,7,10,11-tetrahydrodipyrido[2,1-a:1',2'-k][2,9]phenanthroline-5,12-diium trifluoromethanesulfonate, PDA-C10-13

Starting racemic helquat K (30 mg, 49.0 μmol), 1-methyl-1H-indole-3-carbaldehyde (233.9 mg, 1.47 mmol), piperidine (72 μl, 734.6 μmol) and dry methanol (2 ml) were placed into a 10 ml flask and the resulting mixture was stirred under argon for 6 h at room temperature. Progress of the reaction was monitored by thin layer chromatography. The crude product was precipitated from the reaction mixture by addition of diethylether (30 ml). The suspension was centrifuged and the supernatant was separated from the solid pellet. The solids were dissolved in methanol (1 ml) and the pure product was precipitated by addition of diethylether (30 ml). Then, centrifugation of this suspension, removal of the supernatant and drying of the solid part under vacuum of an oil pump led to 37 mg (41.3 μmol, 84% yield) of a dark-red solid PDA-C10-13.

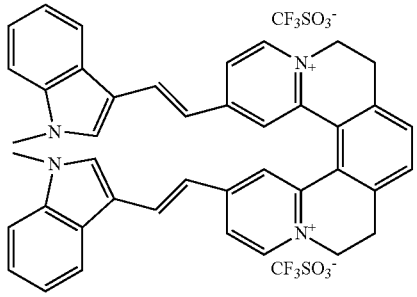

¹H NMR (400 MHz, acetonitrile-d₃): 3.27-3.30 (m, 4H), 3.77 (s, 6H), 4.64-4.68 (m, 2H), 4.76-4.78 (m, 2H), 6.91 (d, J=10.70 Hz, 2H), 7.20-7.23 (m, 214), 7.29-7.32 (m, 2H), 7.43 (d, J=5.47 Hz, 2H), 7.48 (s, 2H), 7.63 (d, J=10.69 Hz, 2H), 7.68 (s, 21-1), 7.80-7.83 (m, 4H), 7.92 (d, J=1.3 Hz, 2H), 8.52 (d, J=4.48 Hz, 2H).

Example 14

8,9-dimethyl-2,15-bis((E)-2-(2-phenyl-1H-indol-3-yl)vinyl)-6,7,10,11-tetrahydrodipyrido[2,1-a:1',2'-k][2,9]phenanthroline-5,12-diium trifluoromethanesulfonate, PDB-C15-8

Starting racemic helquat L (30 mg, 46.8 μmol), 2-phenyl-1H-indole-3-carbaldehyde (310.8 mg, 1.40 mmol), piperidine (69 μl, 702.4 μmol) and dry methanol (2 ml) were placed into a 10 ml flask and the resulting mixture was stirred under argon for 6 h at room temperature. Progress of the reaction was monitored by thin layer chromatography. The crude product was precipitated from the reaction mixture by addition of diethylether (30 ml). The suspension was centrifuged and the supernatant was separated from the solid pellet. The solids were dissolved in methanol (1 ml) and the pure product was precipitated by addition of diethylether (30 ml). Then, centrifugation of this suspension, removal of the supernatant and drying of the solid part under vacuum of an oil pump led to 49 mg (46.8 μmol, 81% yield) of a dark-red solid PDB-C15-8.

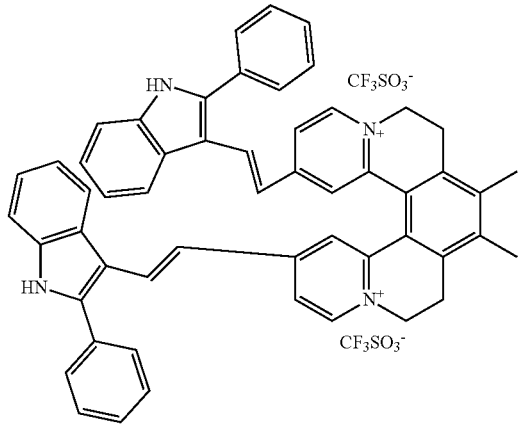

¹H NMR (400 MHz, acetonitrile-d₃): 2.43 (s, 6H), 3.01-3.10 (m, 2H), 3.42-3.46 (m, 2H), 4.52-4.59 (m, 2H), 4.71-4.75 (m, 2H), 7.02 (d, J=16 Hz, 2H), 7.18 (t, J=7.3 Hz, 2H), 7.28 (t, J=7.1 Hz, 2H), 7.38 (d, J=7.4 Hz, 2H), 7.46-7.62 (m, 14H), 7.68 (d, J=1.49 Hz, 2H), 7.87 (d, J=8 Hz, 2H), 8.20 (d, J=6.68 Hz, 2H).

Example 15

8,9-dimethyl-2,15-bis((E)-2-(2-methyl-1H-indol-3-yl)vinyl)-6,7,10,11-tetrahydrodipyrido[2,1-a:1',2'-k][2,9]phenanthroline-5,12-diium trifluoromethanesulfonate, PDB-C10-11

Starting racemic helquat L (30 mg, 46.8 μmol), 2-methyl-1H-indole-3-carbaldehyde (223.6 mg, 1.40 mmol), piperidine (69 μl, 702.4 μmol) and dry methanol (2 ml) were placed into a 10 ml flask and the resulting mixture was stirred under argon for 6 h at room temperature. Progress of the reaction was monitored by thin layer chromatography. The crude product was precipitated from the reaction mixture by addition of diethylether (30 ml). The suspension was centrifuged and the supernatant was separated from the solid pellet. The solids were dissolved in methanol (1 ml) and the pure product was precipitated by addition of diethylether (30 ml). Then, centrifugation of this suspension, removal of the supernatant and drying of the solid part under vacuum of an oil pump led to 38 mg (41.2 μmol, 88% yield) of a dark-red solid PDB-C10-11.

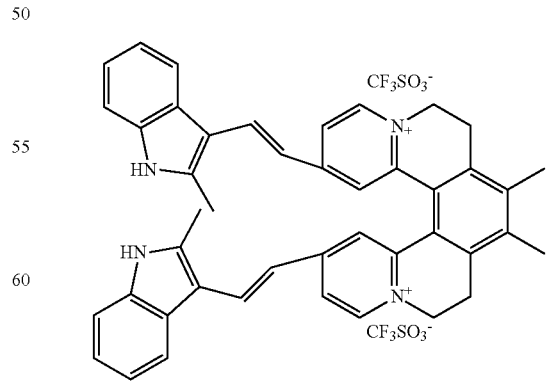

¹H NMR (400 MHz, acetonitrile-d₃): 2.43 (s, 12H), 3.02-3.10 (m, 2H), 3.42-3.46 (m, 2H), 4.60-4.66 (m, 2H), 4.76-4.79 (m, 2H), 6.89 (d, J=16 Hz, 2H), 7.12-7.19 (m, 4H), 7.36 (d, J=8.16 Hz, 2H), 7.63 (d, J=16 Hz, 2H), 7.78-7.85 (m, 6H), 8.46 (d, J=6.74 Hz, 2H).

Example 16

2,15-bis((E)-2-(1H-pyrrolo[2,3-b]pyridin-3-yl)vinyl)-8,9-dimethyl-6,7,10,11-tetrahydrodipyrido[2,1-a:1',2'-k][2,9]phenanthroline-5,12-diium trifluoromethanesulfonate, PDB-C8-14

Starting racemic helquat L (30 mg, 46.8 µmol), 1H-pyrrolo[2,3-b]pyridine-3-carbaldehyde (205.3 mg, 1.40 mmol), piperidine (69 µl, 702.4 µmol) and dry methanol (2 ml) were placed into a 10 ml flask and the resulting mixture was stirred under argon for 6 h at room temperature. Progress of the reaction was monitored by thin layer chromatography. The crude product was precipitated from the reaction mixture by addition of diethylether (30 ml). The suspension was centrifuged and the supernatant was separated from the solid pellet. The solids were dissolved in methanol (1 ml) and the pure product was precipitated by addition of diethylether (30 ml). Then, centrifugation of this suspension, removal of the supernatant and drying of the solid part under vacuum of an oil pump led to 31 mg (34.6 µmol, 74% yield) of a yellow solid PDB-C8-14.

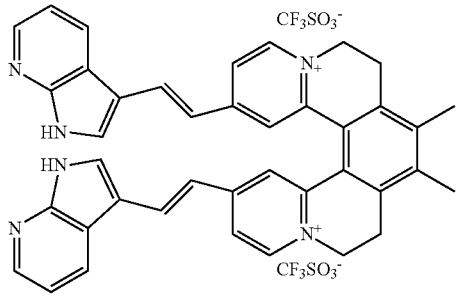

$^1$H NMR (400 MHz, acetonitrile-d$_3$): 2.45 (s, 6H), 3.05-3.12 (m, 1H), 3.42-3.49 (m, 2H), 4.62-4.70 (m, 1H), 4.80-4.85 (m, 2H), 6.94 (d, J=16.21 Hz, 2H), 7.17-7.20 (m, 2H), 7.50 (d, J=16.21 Hz, 2H), 7.68-7.72 (m, 4H), 7.84 (dd, J$_1$=1.34 Hz, J$_2$=6.46 Hz, 2H), 8.20 (dd, J$_1$=1.26 Hz, J$_2$=8.03 Hz, 2H), 8.31-8.32 (m, 2H), 8.54 (d, J=6.79 Hz, 2H).

Example 17

(rac)-2,4,15,17-tetrakis((E)-2-(1H-indol-2-yl)-6,7,8,11,12,13-hexahydro-dipyrido[1,2-a;1',2'-a']benzo[2,1-c:3,4-c']bisazepindiium trifluoromethanesulfonate, PRC-C9-11

Starting racemic helquat Q (10.0 mg, 14.9 µmol), 1H-indole-2-carbaldehyde (138 mg, 957 µmol), pyrrolidine (39 µl, 478 µmol) and dry methanol (0.5 ml) were placed into a 10 ml flask and the resulting mixture was stirred under argon for 1 h at room temperature. Progress of the reaction was monitored by thin layer chromatography. The crude product was precipitated from the reaction mixture by addition of diethylether (5 ml). The suspension was centrifuged and the supernatant was separated from the solid pellet. The solids were dissolved in methanol (0.5 ml) and the pure product was precipitated by addition of diethylether (5 ml). The same procedure was repeated with tetrahydrofuran (0.5 ml) diethylether (5 ml) and acetonitrile (0.3 ml) diethylether (5 ml). Then, centrifugation of this suspension, removal of the supernatant and drying of the solid part under vacuum of an oil pump led to 12.9 mg (10.9 µmol, 73% yield) of a dark-purple solid PRC-C9-11.

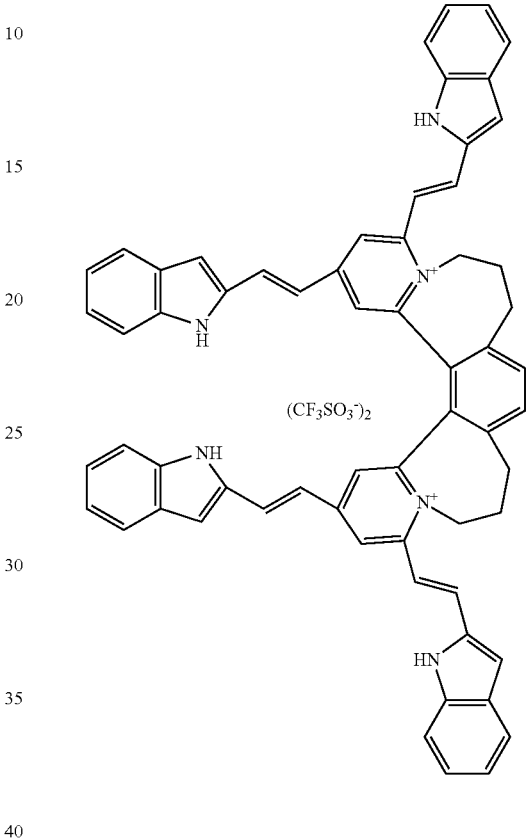

$^1$H NMR (400 MHz, dimethylsulfoxide-d$_6$): 2.31-2.35 (m, 1H), 2.52-2.53 (m, 1H), 2.67-2.78 (m, 1H), 3.11-3.13 (m, 1H), 4.55 (m, 1H), 5.00-5.03 (m, 1H), 6.61 (s, 1H), 6.76 (d, J=1.04 Hz, 1H), 6.866 (s, 1H), 6.97-7.04 (m, 1H), 7.08-7.12 (m, 1H), 7.146 (dd, J=1.28, 8.32 Hz, 1H), 7.15-7.19 (m, 1H), 7.29-7.34 (m, 2H), 7.47 (d, J=7.92 Hz, 1H), 7.53 (dd, J=1.0, 8.96 Hz, 1H), 7.59-7.70 (m, 2H), 7.75 (d, J=16.92 Hz, 1H), 7.82 (d, J=9.72 Hz, 1H), 8.18 (d, J=15.52 Hz, 1H), 8.58 (d, J=1.84 Hz, 1H), 11.61 (s, 1H for NH), 11.90 (s, 1H for —NH).

Example 18

(rac)-2,4,13,15-tetrakis((E)-2-(thiophen-3-yl)vinyl)-6,7,8,11,12,13-hexahydro-dipyrido[1,2-a;1',2'-a']benzo[2,1-c:3,4-c']bisazepindiium trifluoromethanesulfonate, PRC-C5-9

Starting racemic helquat Q (10.0 mg, 14.9 µmol), thiophene-3-carbaldehyde (107 mg, 957 µmol), pyrrolidine (39 µl, 478 µmol) and dry methanol (0.5 ml) were placed into a 10 ml flask and the resulting mixture was stirred under argon for 5 min at room temperature. Progress of the reaction was monitored by thin layer chromatography. The crude product was precipitated from the reaction mixture by addition of diethylether (5 ml). The suspension was centrifuged and the supernatant was separated from the solid pellet. The solids were dissolved in methanol (0.5 ml) and the pure product was precipitated by addition of diethylether (5 ml). The same procedure was repeated with tetrahydrofuran (0.5 ml) diethylether (5 ml) and acetonitrile (0.3 ml) diethylether (5 ml). Then, centrifugation of this suspension, removal of the supernatant and drying of the solid part under vacuum of an oil pump led to 13.1 mg (12.5 µmol, 84% yield) of a yellow solid PRC-C5-9.

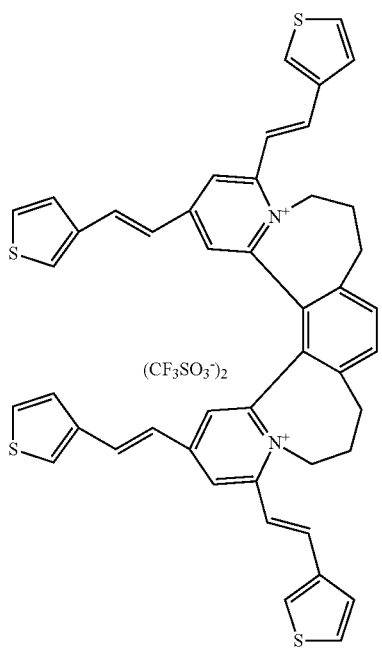 [SMILES: C(=C\c1cc(/C=C/c2ccsc2)[n+]2c(c1)-c1c(ccc3c1-c1cc(/C=C/c4ccsc4)cc(/C=C/c4ccsc4)[n+]1CCC3)CCC2)/c1ccsc1 ; "(CF3SO3-)2"]

$^1$H NMR (400 MHz, acetonitrile-d$_3$): 2.32-338 (m, 1H), 2.45-2.54 (m, 1H), 2.67-2.72 (m, 1H), 3.01-3.06 (dd, J=6.44, 14.04 Hz, 1H), 4.24-4.32 (td, J=5.32, 14.04 Hz, 1H), 5.013 (dd, J=5.72, 14.68 Hz, 1H), 6.97 (d, J=16.28 Hz, 1H), 6.98 (d, J=1.96 Hz, 1H), 7316 (d, J=15.8 Hz, 1H), 7.37 (dd, J=1.28, 5.16 Hz, 1H), 7.48 (dd, J=2.80, 5.08, 1H), 7.60 (dd, J=2.88, 5.16 Hz, 1H), 7.65-7.71 (m, 4H), 7.83 (d, J=15.76 Hz, 1H), 7.88 (dd, J=1.24, 2.88 Hz, 1H), 8.24 (d, J=2.04, 1H).

Example 19

(rac)-2,4-bis((E)-2-(1-methyl-1H-pyrrol-2-yl)vinyl)-6,7,10,11-tetrahydro-dipyrido[2,1-a:1',2'-k][2,9]phenanthroline-5,12-diium trifluoromethanesulfonate, HTA-C6-4

Starting racemic helquat O (10.0 mg, 16.3 µmol), 1-methyl-1H-pyrrole-2-carbaldehyde (57 mg, 522 µmol), pyrrolidine (22 µl, 261 µmol) and dry methanol (0.5 ml) were placed into a 10 ml flask and the resulting mixture was mixed under argon for 1 h at room temperature. Progress of the reaction was monitored by thin layer chromatography. The crude product was precipitated from the reaction mixture by addition of diethylether (5 ml). The suspension was centrifuged and the supernatant was separated from the solid pellet. The solids were dissolved in methanol (0.5 ml) and the pure product was precipitated by addition of diethylether (5 ml). The same procedure was repeated with tetrahydrofuran (0.5 ml) diethylether (5 ml) and acetonitrile (0.3 ml) diethylether (5 ml). Then, centrifugation of this suspension, removal of the supernatant and drying of the solid part under vacuum of an oil pump led to 10.1 mg (12.7 µmol, 78% yield) of an orange solid HTA-C6-4.

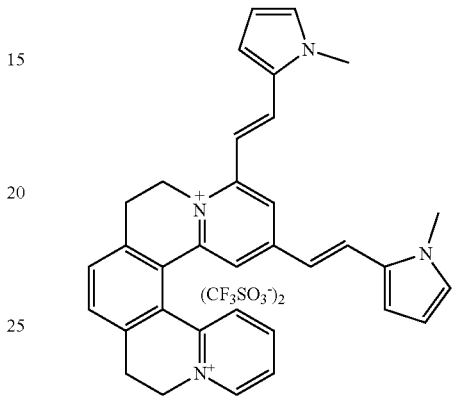

$^1$H NMR (400 MHz, acetonitrile-d$_3$): 3.08-3.33 (m, 4H), 3.68 (s, 3H), 3.84 (s, 3H), 4.22-4.26 (m, 1H), 4.89-4.90 (m, 2H), 5.02-5.05 (m, 1H), 6.17-6.19 (m, 1H), 6.26-6.28 (m, 1H), 6.73 (d, J=16.4 Hz, 1H) 6.71 (t, 1.6 Hz, 1H), 6.91 (t, J=2.04 Hz, 1H), 6.98-7.00 (m, 2H), 7.13 (d, J=15.56 Hz, 1H), 7.37 (d, J=15.96 Hz, 1H), 7.44 (d, J=1.96, 1H), 7.16-7.71 (m, 3H), 7.85 (td, J=1.44, 2.96, 7.64 Hz, 1H), 7.99 (dd, J=1.4, 8.48 Hz, 1H), 8.08 (d, J=1.96 Hz, 1H), 8.15 (td, J=1.48, 1.92, 8.48 Hz, 1H), 8.78 (dd, J=1.36, 5.6817.16 Hz, 1H).

Example 20

(rac)-2,4-bis((E)-2-(4-methyl-1H-imidazol-5-yl)vinyl)-6,7,10,11-tetrahydro-dipyrido[2,1-a:1',2'-k][2,9]phenanthroline-5,12-diium trifluoromethanesulfonate, HTA-C5-11

Starting racemic helquat O (10.0 mg, 16.3 µmol), 1-methyl-1H-pyrrole-2-carbaldehyde (57 mg, 522 µmol), pyrrolidine (22 µl, 261 µmol) and dry methanol (0.5 ml) were placed into a 10 ml flask and the resulting mixture was stirred under argon for 1 h at room temperature. Progress of the reaction was monitored by thin layer chromatography. The crude product was precipitated from the reaction mixture by addition of diethylether (5 ml). The suspension was centrifuged and the supernatant was separated from the solid pellet. The solids were dissolved in methanol (0.5 ml) and the pure product was precipitated by addition of diethylether (5 ml). The same procedure was repeated with tetrahydrofuran (0.5 ml) diethylether (5 ml) and acetonitrile (0.3 ml) diethylether (5 ml). Then, centrifugation of this suspension, removal of the supernatant and drying of the solid part under vacuum of an oil pump led to 10.1 mg (12.7 μmol, 78% yield) of dark-yellow solid HTA-C5-11.

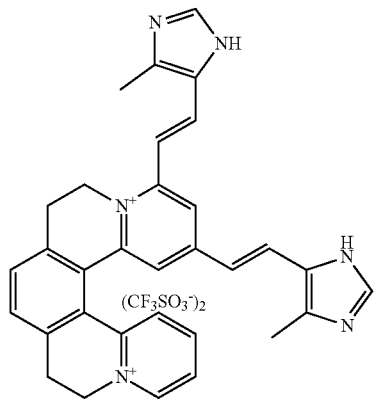

$^1$H NMR (400 MHz, acetonitrile-d$_3$): 2.32 (s, 3H), 2.46 (s, 3H), 3.12-3.43 (m, 4H), 4.27-4.31 (m, 1H), 4.80-4.88 (m, 2H), 5.05 (m, 1H), 7.01 (d, J=16.04 Hz, 1H), 7.44-7.52 (m, 4H), 7.62-7.76 (m, 4H), 7.83-7.96 (m, 2H), 8.13-8.17 (m, 1H), 8.026 (d, J=1.96 Hz, 1H), 8.77 (dd, J=2.12, 6.32 Hz, 1H), 10.38 (broad s, 2H for —N$\underline{H}$).

Example 21

2,4,13,15-tetrakis((E)-2-(1-methyl-1H-indol-3-yl)vinyl)-6,7,10,11-tetrahydrodipyrido[2,1-a:1',2'-k][2,9]phenanthroline-5,12-diium trifluoromethanesulfonate, TKA-C10-13

Starting helquat P (10 mg, 15.6 μmol), 1-methyl-1H-indole-3-carbaldehyde (149.1 mg, 936.6 μmol), pyrrolidine (41 μl, 499.5 μmol) and dry methanol (0.5 ml) were placed into a 10 ml vial with screw cap and the resulting mixture was stirred under argon for 45 min at room temperature. Progress of the reaction was monitored by thin layer chromatography. The crude product was precipitated from the reaction mixture by addition of diethylether (5 ml). The suspension was centrifuged and the supernatant was separated from the solid pellet. The solids were dissolved in tetrahydrofuran (0.3 ml) and the product was precipitated by addition of diethylether (5 ml). Then, the suspension was centrifuged and the supernatant was separated. This procedure was repeated three more times using methanol (0.5 ml) instead of tetrahydrofuran and two more times using just diethylether (5 ml). Then, the solid product was dried under vacuum of an oil pump. In this way, 12.3 mg (10.2 pilot, 65% yield) of a dark-red solid was obtained TKA-C10-13.

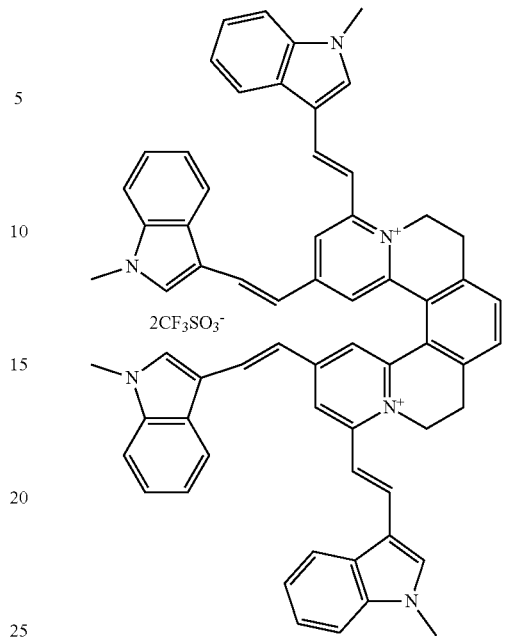

$^1$H NMR (400 MHz, dimethylsulfoxide-d$_6$): 3.23-3.41 (m, 4H), 3.72 (s, 6H), 3.97 (s, 6H), 4.54 (t, J=12.4; 12.4 Hz, 2H), 5.24 (d, J=11.1 Hz, 2H), 6.93 (dd, J=15.1; 0.1 Hz, 2H), 6,95 (d, J=16.2 Hz, 2H), 7.13 (ddd, J=8.2; 7.2; 1.1 Hz, 2H), 7.33-7.42 (m, 4H), 7.45 (d, J=8.4 Hz, 2H), 7.53 (d, J=16.7 Hz, 2H), 7.65-7.70 (m, 6H), 7.77-7.79 (m, 4H), 8.07 (d, J=1.8 Hz, 2H), 8.19-8.23 (m, 6H), 8.30 (d, J=1.9 Hz, 2H).

Methods for Biological Characterization of Substances

Quantification of the Extent of Interaction of Helquats with G-Quadruplexes in Model Oligonucleotides Using the FRET Method To determine the degree of in vitro interactions of helquats with G-quadruplex(es), the oligonucleotides containing the guanine-rich sequences of human telomere (F21T) and NHE III$_1$ promoter region of c-myc oncogene (Fmyc27T) were used. Both oligonucleotides capable of forming an intramolecular G-quadruplex were end-labeled with suitable fluorophores so as to form donor-acceptor FRET pair (5'-FAM and 3'-TAMRA). If the oligonucleotide is folded into the structure of the G-quadruplex, donor is in close proximity of acceptor and radiationless energy transfer to the acceptor occurs. With increasing temperature of the reaction mixture G-quadruplex structure gradually denatures and thus the donor and acceptor (FAM-TAMRA) drift apart. This leads to an increase in fluorescence of donor (FAM) and a decrease in fluorescence of acceptor (TAMRA).

The result of measurement is the curve of dependence of the intensity of fluorescence of the donor on the temperature. If the G-quadruplex is stabilized by ligand, melting temperature will increase. Melting temperature of G-quadruplex corresponds to the temperature when 50% of the original amount of the folded G-quadruplex is denatured. The measurement outcome is the difference in the melting temperatures ($\Delta T_m$) of the G-quadruplex alone and the G-quadruplex stabilized by ligand. In case of Fmyc27T experiments were performed in cacodylate buffer (10 mmol·l$^{-1}$, pH=7.2) with KCl (5 mmol·l$^{-1}$) and LiCl (95 mmol·l$^{-1}$) oligonucleotide and in case of F21T oligonucleotide in cacodylate buffer (10 mmol·l$^{-1}$, pH=7.2) with KCl (25 mmol·l$^{-1}$) and LiCl (75 mmol·l$^{-1}$).

Both oligonucleotides were denatured for 5 minutes at 95° C. and subsequently allowed to cool to room temperature (3 hours) in the switched-off thermoblock. The final oligonucleotide concentration in the reaction mixture was 0.2 $\mu mol \cdot l^{-1}$. Test helquats were present at concentrations of 1 $\mu mol \cdot l^{-1}$. The total reaction volume was 30 µl. The melting temperature of the oligonucleotides alone (without the presence of helquats) under these conditions was 58.1±0.2° C. for F21T and 64.7±0.4° C. for Fmyc27T. For determining the selectivity of binding of helquats to G-quadruplex in comparison with the double-stranded DNA, 50-fold excess of double-stranded DNA (10 mmol·l$^{-1}$ unlabeled competitor ds26 forming a hairpin) is added to the reaction mixture. After the addition to the reaction mixture ds26 competes with labeled oligonucleotide (Fmyc27T or F21T) for ligand binding. If the test ligand is selective for the G-quadruplex, the presence of ds26 competitor does not decrease $\Delta T_m$ compared to $\Delta T_m$ measured without ds26 competitor. Melting temperature of oligonucleotides alone in the presence of the competitor is 59.4±0.5° C. for F21T and 66.3° C.±0.6° C. for Fmyc27T.

Fluorescence of FAM donor was measured using real-time PCR apparatus Opticon 2 (excitation 470-505 nm and emission 523-543 nm) in temperature increments of 0.5° C. in the range 25 to 95° C. Evaluation of the sigmoid curves of fluorescence intensity dependent on the temperature were performed in GraphPad Prism 5 (GraphPad Software, Inc., USA). Using nonlinear five parametric regression the inflection point on the curve was calculated that corresponds to the melting temperature ($T_m$) of the G-quadruplex under the given conditions. The values were obtained from at least three independent measurements.

```
ds26:
5'-CAATCGGATCGAATTCGATCCGATTG-3'

F21T:
5'-FAM-GGGTTAGGGTTAGGGTTAGGG-TAMRA-3'

Fmyc27T:
5'-FAM-TGGGGAGGGTGGGGAGGGTGGGGAAGG-TAMRA-3'
```

TABLE 1

Change of the melting temperature of G-quadruplex oligonucleotide Fmyc27T in the presence of different ligands; values are determined by FRET method

| Compound designation | $\Delta T_m$ (° C.) Fmyc27T | SD Fmyc27T | $\Delta T_m$ (° C.) Fmyc27T/ds26 | SD Fmyc27T/ds26 |
|---|---|---|---|---|
| LSA-C9-30 | 10.5 | 0.4 | 8.2 | 0.4 |
| LSA-C9-32 | 10.4 | 0.5 | 8.1 | 0.2 |
| MJA-C13-8 | 11.0 | 1.1 | 4.9 | 1.2 |
| MJB-C8-27 | 9.7 | 1.0 | 10.0 | 1.3 |
| MSB-C13-8 | 12.6 | 0.2 | 7.7 | 0.9 |
| PDA-C10-11 | 14.9 | 0.4 | 13.9 | 0.7 |
| PDA-C10-13 | 13.8 | 0.9 | 13.6 | 1.1 |
| PDA-C15-8 | 18.8 | 1.3 | 19.9 | 0.4 |
| PDA-C8-27 | 11.8 | 0.6 | 9.6 | 0.3 |
| PDA-C9-30 | 14.6 | 0.8 | 16.0 | 1.1 |
| PDB-C10-11 | 14.2 | 0.9 | 13.1 | 1.1 |
| PDB-C15-8 | 15.7 | 1.5 | 14.5 | 1.3 |
| PDB-C8-14 | 11.5 | 0.7 | 9.3 | 0.7 |
| PRA-C12-5 | 11.3 | 0.2 | 8.6 | 0.5 |

TABLE 2

Change of melting temperature of G-quadruplex oligonucleotide F21T in the presence of different ligands; values are determined by FRET method

| Compound designation | $\Delta T_m$ (° C.) F21T | SD F21T | $\Delta T_m$ (° C.) F21T/ds26 | SD F21T/ds26 |
|---|---|---|---|---|
| PDA-C10-11 | 12.9 | 0.2 | 12.3 | 0.4 |
| PDA-C10-13 | 9.7 | 1.2 | 9.1 | 0.3 |
| PDA-C15-8 | 17.2 | 1.2 | 17.3 | 1.0 |
| PDA-C9-30 | 12.3 | 2.0 | 13.1 | 2.0 |
| PDB-C10-11 | 13.0 | 0.8 | 10.7 | 1.0 |
| PDB-C15-8 | 11.3 | 1.2 | 11.1 | 1.2 |
| PDB-C8-14 | 8.4 | 1.0 | 5.0 | 0.1 |
| LSA-C9-30 | 8.6 | 0.4 | 5.5 | 0.9 |
| LSA-C9-32 | 9.3 | 0.1 | 6.6 | 0.2 |
| MJA-C13-8 | 7.4 | 0.1 | 1.4 | 1.0 |
| MJB-C8-27 | 8.0 | 0.8 | 5.2 | 0.8 |
| MSB-C13-8 | 9.0 | 0.3 | 3.4 | 0.3 |
| PDA-C8-27 | 9.3 | 0.5 | 7.0 | 0.6 |
| PRA-C12-5 | 8.8 | 0.3 | 5.4 | 0.7 |

Melting temperature values of c-myc promoter (Fmyc27T) and telomeric (F21T) G-quadruplex (Tab. 1 and Tab. 2) indicate the unexpectedly significant ability of test substances to stabilize these structures. Simultaneously, helquats have significantly higher selectivity for G-quadruplexes compared with the double-stranded DNA than positive control TMPyP4.

Quantification of Interaction of Helquats with G-Quadruplex in Model Oligonucleotides Using ECD Method ECD Spectrometer ECD spectra were measured on J-815 spectrometer (Jasco, Japan). Measurement settings (Tab. 3), spectra saving and background subtraction was performed in a Spectra Manager software (Jasco, Japan).

TABLE 3

Setting of the parameters for ECD spectra and melting curve measurement at a selected wavelength

| Parameter | Settings spectrum | melting curve |
|---|---|---|
| beginning | 800 nm | 25° C. |
| end | 210 nm | 95° C. |
| band width | 1 nm | 1 nm |
| response | 1 sec | 1 sec |
| sensitivity | standard | standard |
| increment | 1 nm | 1° C. |
| scan speed | 200 nm min$^{-1}$ | — |
| accumulation | 5 | — |
| monitored wavelength | — | 263 nm |
| temperature step | — | 1° C. · min$^{-1}$ |

For measurement of the temperature dependencies the cuvettes in the cuvette compartment were placed in the Peltier module, the temperature was controlled by the Spectra Manager software. Melting curves were measured at a wavelength which corresponds to the maximum difference in signal intensity of ECD spectra of oligonucleotide at 25 and 95° C., as shown in FIG. 1. Before and after measuring the melting curves, ECD spectra in extreme temperatures were measured, in order to verify the stability of the studied system.

ECD Spectra Processing

Processing of the spectra was performed using Spectra Manager (Jasco, Japan). The resulting spectra were obtained from the measured sample spectrum after subtraction of background spectrum, which was spectrum of the solvent.

Measuring of sample spectrum and background was conducted under identical conditions. ECD spectra are reported as ellipticity, labeled in the CD figures [mdeg], whose numerical value is associated with dimensionless circular dichroism $\Delta A$ ($CD_v$=32980 $\Delta A_v$). This CD notations preserves conventions of the international journals in which articles from the field are published.

Oligonucleotide Solutions

Stock solution of 100 mol l$^{-1}$ was prepared from c-Myc27 oligonucleotide by dissolution in $H_2O$. The cuvette of 1 mm thickness was filled with 7 μl of oligonucleotide solution and 133 μl of Li$^+$-cacodylate buffer. Oligonucleotide solution in the cuvette was overlayed with mineral oil to measure temperature dependencies without concentration changes due to evaporation of the solvent at higher temperatures.

```
c Myc27:
5'-TGGGGAGGGTGGGGAGGGTGGGGAAGG-3'
```

The Ligand Solutions

From stock solutions of the racemic ligands in DMSO at a concentration of 10 mol·l$^{-1}$ solutions were prepared at a concentration of 140 μmol l$^{-1}$ by dissolving in $H_2O$. Ligands were added to the solution of oligonucleotide under buffer/mineral oil interface using Hamilton microsyringe (5 μl of solution at a concentration of 140 mol·l$^{-1}$). The resulting molar ratio of oligonucleotide:ligand was 1:1.

The Measurement Procedure

The cuvette filled with c-Myc27 oligonucleotide solution in Li$^+$-cacodylate buffer ($c_{c\text{-}Myc27}$=5 μmol l$^{-1}$) was first heated for 5 minutes at 95° C., at this temperature ECD spectrum was measured. Then the sample was cooled to 25° C., allowed to stabilize for 10 min and then ECD spectrum was measured again. Then, the melting curve of ECD oligonucleotide at 263 nm was measured in the temperature range 25-95° C. and for verification of the stability of the sample spectra the spectra were measured again at 95 and 25° C. Under the oil layer ligand solution ($c_{ligand}$=5 μmol l$^{-1}$) was added to a solution of oligonucleotide, the sample was thoroughly mixed and ECD spectrum measured at 25° C., the melting curve was obtained and again control spectra were measured at 95 and 25° C.

Results

In FIG. 1, the spectra of ECD oligonucleotide c-Myc27 in Li$^+$-cacodylate buffer ($c_{c\text{-}Myc27}$=5 μmol l$^{-1}$) at 25 and 95° C. are shown. At 25° C., the bands 210(+), 240(−), and 263(+) were observed. This spectral profile corresponds to parallel G-quadruplex conformations [Vorlickova M. et al. (2012) *Methods*, 57, 64; Sun, D. et al. (2010) *Methods in Molecular Biology*, 608, 65; Yang D., et al. (2010) *Future Med. Chem.*, 2, 619]. Based on the similarity of ECD spectra it is suggested that even at 95° C. the solution contains a structure of parallel G-quadruplex. After measuring the melting curve (sigmoidal shape, FIG. 2), however, it became evident that with increasing temperature the G-quadruplex unfolds. Maintaining ECD signal profile, especially the presence of the band at 263 nm corresponds to the interaction of neighboring bases in the oligonucleotide chain [Cyprus, J. et al. (2002) *Biopolymers*, 67, 275; Cyprus J. et al. (2007) *Biopolymers*, 87, 218; Kejnovská et al. (2007) *Biopolymers*, 85, 19].

Interaction G-Quadruplex/Ligand: Thermal Experiment

Figure 2:
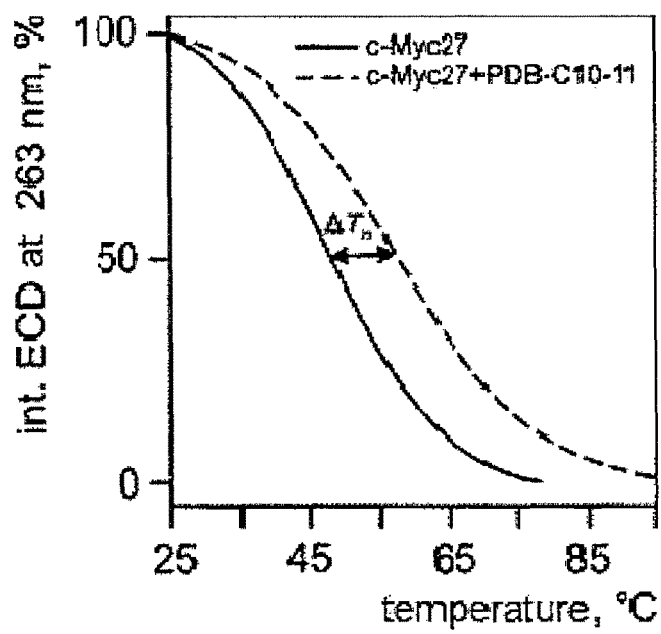
FIG. 2 shows dependence of ECD intensity (detected at 263 nm) on temperature of solution of oligonucleotide c-Myc27 in the presence of the ligand PDB-C10-11 (molar ratio oligonucleotide:ligand=1:1).

Decomposition of the G-quadruplex structure in the presence of ligands under influence of temperature was monitored at the wavelength corresponding to the maximum difference in signal intensities of ECD oligonucleotide/ligand at 25 and 95° C., i.e. at 263 nm. Thermal stability of G-quadruplex was monitored in the range of 25 to 95° C. and in a molar ratio of oligonucleotide:ligand=1:1. Example of influence of the studied ligand on the stability of G-quadruplex formed from c-Myc27 oligonucleotide is shown in FIG. 2. This figure shows the increase in melting temperature in the presence of G-quadruplex ligand PDB-C10-11.

The degree of G-quadruplex stabilization was expressed as change of melting temperature caused by the presence of G-quadruplex ligands ($\Delta T_m$):

$$\Delta T_m = T_{m,oligonucleotide+ligand} - T_{m,oligonucleotide} \quad (1),$$

where $T_{m,oligonucleotide+ligand}$ is melting temperature of molecular system comprising the oligonucleotide and the ligand and $T_{m,oligonucleotide}$, the melting temperature of the oligonucleotide itself. Tab. 4 summarizes the changes in melting temperatures of c-Myc27 oligonucleotide G-quadruplex in the presence of studied ligands.

TABLE 4

Change of melting temperatures of c-Myc27 oligonucleotide G-quadruplex in the presence of various ligands; values are determined by ECD

| Compound designation | $\Delta T_m$ (° C.) |
|---|---|
| MJA-C13-8 | 6.8 |
| PDB-C10-11 | 9.8 |
| PDB-C8-14 | 5.0 |
| PDA-C15-8 | 10.1 |
| LSA-C9-30 | 6.4 |
| PDA-C10-11 | 8.2 |

Results of this part of study show that helquats cause a surprisingly high degree of stabilization of the G-quadruplex. These results also document sensitivity of ECD spectroscopy to secondary structures of oligonucleotides and show that by measurement of ECD melting curves the ability of ligands to stabilize G-quadruplex may be characterized.

Stabilization of G-Quadruplex in Promoter Region of the c-Myc Gene

A dual luciferase analysis was used to determine the degree of stabilization of G-quadruplex in a promoter region of the c-myc gene on cellular level. Stabilization of G-quadruplex is expressed as the ratio of expression of two luciferases (firefly and Renilla) from the co-transfected vectors pGL4.10-myc (luc2) and pRL-TK (Renilla) into a cell line HGC-27 expressing c-myc protein. Expression of the reporter gene (firefly luciferase) from pGL4.10-myc vector is controlled by the c-myc regulatory region of a length of 860 by (in the range from −306 to +554). The inserted sequence contains NHE III$_1$ segment which forms G-quadruplex [Yang, D. et al. (2010) Future Med Chem., 2, 619], and is responsible for as much as 90% of the transcriptional activity of the c-myc gene.

Level of expression of firefly luciferase reporter gene corresponds to promoter activity of c-myc and thus to the degree of stabilization of the G-quadruplex. The signal is normalized to Renilla luciferase expression from pRL-TK vector under the control of a constitutive viral thymidine kinase (HSV-TK) promoter. The amount of Renilla luciferase expression serves as an internal control for normalization of firefly signal on transfection efficiency in the sample. Plasmids pGL4.10-myc (luc2) and pRL-TK were propagated in *Escherichia coli* (DH5α strain) and purified using the Qiagen Plasmid Mini and Midi kits. Cells were cultured under standard conditions and in exponential growth phase were seeded into a white 96-well microtiter plates. Transfection was carried out using a transfection reagent X-tremeGENE HP DNA in OptiMEM media for two hours. The ratio of reporter and control vector was 1:1 and the ratio of transfection reagent to the total amount of DNA was 1:1. Two hours after transfection helquats were added in a concentration of 50 µmol·l$^{-1}$. Quantity of firefly and Renilla luciferases in the samples was determined 24 hours after transfection. Dual luciferase analysis was performed using a commercially available kit (Promega, cat. No. E1960) according to manufacturer's instructions. Luminescence was measured using a luminometer EnSpire Alpha Plate Reader. The data obtained were normalized to the Renilla luciferase signal and then the values were related to control. Results of stabilization of G-quadruplex and inhibition of the expression of firefly luciferase are summarized in Table 5. Table 6 shows the concentration dependence for two selected helquats (MJA-C13-8 and C13-6-VDJA).

TABLE 5

Results of inhibition studies of luciferase expression in dual luciferase analysis with plasmid pGL4.10-myc (luc2) at helquats concentration of 50 µmol · l$^{-1}$ relative to control (control = 100%)

| Compound designation | 50 µmol · l$^{-1}$ [%] |
|---|---|
| VDJA-C13-6 | 27 |
| VDJA-C13-8 | 76 |
| LSA-C13-8 | 58 |
| MJA-C9-30 | 55 |
| MSC-C10-11 | 74 |
| MSC-C9-30 | 68 |
| MJA-C13-8 | 56 |
| MJB-C5-9 | 75 |
| MSC-C9-10 | 56 |
| MJB-C5-3 | 65 |
| LSA-C9-32 | 74 |
| HTA-C5-9 | 85 |
| MJA-C8-28 | 72 |
| MSC-C15-8 | 76 |
| MJB-C8-27 | 88 |
| MSC-C13-16 | 85 |
| MSC-C10-10 | 85 |
| PRA-C12-5 | 86 |
| PDA-C8-27 | 77 |

TABLE 6

Concentration dependence of inhibition of luciferase expression in dual luciferase analysis with plasmid pGL4.10-myc (luc2) for helquats MJA-C13-8 and VDJA-C13-6 relative to control (control = 100%)

| Compound designation | Concentration (µmol · l$^{-1}$) | Quantification of expression relative to control (%) |
|---|---|---|
| MJA-C13-8 | 10 | 79.3 ± 6.7 |
| | 50 | 69.8 ± 6.0 |
| | 150 | 57.9 ± 2.5 |
| VDJA-C13-6 | 10 | 59.0 ± 17.9 |
| | 50 | 27.1 ± 0.8 |
| | 150 | 15.3 ± 2.9 |

Immunodetection of Protein c-Myc

Determination of changes in c-myc protein expression (transcription factor) in cell lysates prepared from tumor cell line HGC-27 after treatment with test helquats (Tab. 7) was carried out by immunodetection after separation of proteins according to their size by gel electrophoresis (SDS-PAGE) and blotting.

To determine the influence helquats on expression of c-myc protein, the cells were cultured under standard conditions and in the exponential growth phase were seeded into flasks at a density of 25,000 cells/cm$^2$. The next day selected helquats were added at a concentration of 50 µmol·l$^{-1}$. After 24 hour incubation, the cell pellets were obtained and, after addition of RIPA buffer with protease inhibitors (PrIC) and phosphatases (PhIC) (for composition see Tab. 8) cell lysates were prepared. 150 µl of RIPA buffer was used for 10$^7$ cells. Protein concentrations in the lysates were measured by BCA method. Separation of proteins in the lysates was carried out on a 12% denaturing polyacrylamide gel. The separated proteins were transferred to PVDF membrane by Western blotting.

Incubation with primary mouse monoclonal antibody against the protein c-myc (dilution 1:1000 in "SignalBoost" reagent) was carried out overnight at 4° C., and then with the primary mouse anti-β-actin (1:5000 dilution in 5% milk in TBS-T buffer) at room temperature for 2 hours. Subsequently, the secondary horse monoclonal antibody conjugated to horseradish peroxidase (diluted 1:2000 in 5% milk in TBS-T buffer) binding to mouse IgG antibody was applied. C-myc proteins and β-actin bound to the membrane were visualized using detection kit (SuperSignal® West Femto Maximum Sensitivity Substrate, Cat. No. 34095, Thermo Fisher Scientific, Inc., USA) in the chemiluminescence detection system ImageQuant LAS 4000 Mini (Cat. No. 28-9558-13, GE Healthcare Life Sciences, USA). The amount of protein was quantified by densitometry in Quantity One software. The amount of c-myc in the samples was normalized to β-actin, and subsequently related to a control sample.

TABLE 7

Tested helquats; results of inhibition of c-myc protein expression relative to control (control = 100%) at a total concentration of 50 µmol · l$^{-1}$

| Compound designation | 50 µmol · l$^{-1}$ [%] |
|---|---|
| MSC-C9-30 | 14 |
| LSA-C13-8 | 15 |
| MJB-C5-11 | 23 |
| MJA-C8-28 | 23 |
| LSA-C9-16 | 28 |
| MJB-C5-9 | 30 |
| MSC-C9-18 | 31 |
| HTA-C9-16 | 32 |
| PRC-C5-9 | 34 |
| MSC-C9-16 | 36 |
| HTA-C9-17 | 44 |
| MJA-C13-8 | 58 |
| MSC-C15-8 | 58 |
| MJA-C11-25 | 66 |
| PRC-C10-10 | 71 |
| HTA-C10-10 | 75 |
| VDJA-C13-8 | 77 |
| PDA-C5-11 | 80 |
| MJA-C19-4 | 81 |
| PDB-C13-8 | 83 |
| MSC-C10-36 | 85 |

TABLE 8

Lysis buffer composition

RIPA buffer:

50 mmol · l$^{-1}$ TRIS-HCl
1% Nonidet-40

TABLE 8-continued

Lysis buffer composition 150 mmol · l$^{-1}$ NaCl
0.5% sodium deoxycholate
0.1% SDS
protease a phosphatase inhibitors:

PrIC 2.5 µl/100 µl RIPA buffer
PhIC 1 µl/100 µl RIPA buffer

Determination of Viability Using XTT Assay

Effect of test compounds on viability (proliferation) of the selected cell lines was examined at concentrations from 0 to 100 mmol·l$^{-1}$.

Characterization of the Cell Lines Used

To assess the antiproliferative effects of the tested substances in vitro, tumor cell line CCRF-CEM derived from acute lymphoblastic leukemia and normal (healthy) HUVEC endothelial cells from umbilical vein were used. Both of these cell lines were cultured under optimal conditions for their growth in the appropriate medium in plastic bottles or plastic Petri dishes of various sizes (TPP, BD Biosciences) at 37° C., 5% $CO_2$ and 95% humidity. HUVEC cells were purchased from BD Biosciences. CCRF-CEM cell line was obtained from ATCC/LGC Standards (American Type Cell Collection).

CCRF-CEM (Cat. No. ATCC CCL-119)

Suspension cell line CCRF-CEM is a continuous in vitro culture of acute lymphoblastic leukemia. Cell line CCRF-CEM was grown in RPMI 1640 medium (Sigma-Aldrich, cat. No. R8758) supplemented with 2 mmol·l$^{-1}$ glutamine (Invitrogen, cat. No. 35050-038), 10% fetal bovine serum (FBS; Sigma-Aldrich, cat. No. F9665), 100 IU/ml penicillin, 100 µg/ml streptomycin (Sigma-Aldrich, cat. No. P0781). Passaging was carried out 2-3 times a week. Population doubling time of CCRF-CEM cells under the used culture conditions is 20 hours.

HUVEC (BD Biosciences, Cat. No. 354151)

Normal human endothelial cells from the umbilical vein are adherent cells, which were grown in plastic Petri dishes coated with collagen I. The culture medium (E-STIMTM; BD Biosciences, cat. No. 355054) already containing 2% FBS (fetal bovine serum) hydrocortisone and heparin was further supplemented with epidermal growth factor (EGF, 5 mg) and factors promoting growth of endothelial cells (ECGS, 100 mg). The culture medium did not contain antibiotics. Cells were passaged after reaching 90% confluence by incubation with 0.25% solution of trypsin-EDTA (1 ml, 3 min; 37° C.). Then, 5 ml of complete culture media E-STIM™ was added and the cells were centrifuged (180×g, 7 minutes), resuspended and transferred in a desired amount in a new Petri dish with fresh medium. In the experiments cells between passages 3 and 8 (after thawing) were used. Population doubling time of HUVEC cells under the used culture conditions is 38 hours.

Evaluation of the Viability of Cancer and Normal Cells Treated with Different Concentrations of Test Substances For testing of the sensitivity of cell lines to studied helquats XTT cytotoxicity/proliferation assay for determination of cell viability was used. This method is based on the ability of metabolically active cells to reduce the yellow tetrazolium salt XTT to orange formazan. The rate of conversion is measured as the increase in absorbance at 492 nm and is proportional to the enzymatic activity of mitochondrial dehydrogenases and thus the number of metabolically active (viable) cells. The output is the $IC_{50}$ value corresponding to the concentration of the test substance that causes a decrease in the number of viable cells by half (i.e. 50% slowdown of cell division) relative to the control, untreated population. Thus it reflects the effectiveness of the test substance towards the tested cell line.

Cells in exponential growth phase were plated into 96-well microtiter plate at a concentration of 3000 cells per well. Each well contained 90 µl of cell suspension. The following day, 10 µl of 10× concentrated test substances was added. Effect of helquats has been studied in the concentration range 1-100 µmol·l$^{-1}$ (or 1, 2.5, 5, 7.5, 10; 15; 25; 50 and 100 µmol·l$^{-1}$). In addition to the part of the plate containing the mentioned dilutions of test compounds there were always two control columns present, first column with medium alone (i.e. blank) and the second column with the cells in medium without test compounds (control). Into the blank and control wells the same volume of solvent (water) as the volume of the substances was added. After 72 hours of treatment with substances the measurement of viability was performed according to the manufacturer instructions. Briefly, into each well of a 96-well microtiter plate 50 µl of the prepared working solution of XTT (detection reagent) was added and then the microtiter plate was returned to the $CO_2$ incubator. After 2 hours, the absorbance of each well at 492 nm (reference wavelength 690 nm) was measured using a multifunctional microplate reader (Tecan Genios, Austria).

Working XTT solution was prepared by mixing 5 ml XTT reagent and 100 µl PMS solution.

Preparation of the two components is shown below:

XTT Reagent

XTT solution was prepared by dissolving 500 mg of the XTT sodium salt (Sigma-Aldrich, cat. No. X4626) in 500 ml RPMI-1640 medium (Sigma-Aldrich, cat. No. R7509), and subsequent heating for 10 min at 60° C. From the prepared solution 5 ml aliquots were prepared and stored at −20° C. Before use, an aliquot of solution was thawed in a water bath at 37° C.

PMS Solution (Phenazine Methosulfate)

PMS solution was prepared by dissolving 0.383 mg PMS (Sigma-Aldrich, cat. No. P9625) in 1 ml of phosphate buffer (PBS). The 100 ml aliquots were stored at −20° C.

The results of determination of the viability of cancer and normal cells after treatment with different concentrations of test substances are summarized in Table 9. The $IC_{50}$ value is the concentration of test compound that caused a 50% decrease in the number of viable cells (cell growth inhibition) after 72 hours of treatment. Each concentration of a helquat was tested in triplicates within one $IC_{50}$ value determination. Each of these $IC_{50}$ value determinations was repeated in at least three independent experiments. Values above 100 µmol·l$^{-1}$ were obtained by extrapolation of data measured in the concentration range 0-100 µmol·l$^{-1}$ of helquats.

TABLE 9

| Compound designation | $IC_{50}$ | |
|---|---|---|
| | CCRF CEM | HUVEC |
| MSC-C13-16 | **** | ≥100 |
| MSC-C9-30 | **** | ≥100 |
| MJA-C13-22 | **** | ≥100 |
| MSC-C9-16 | **** | ≥100 |
| MSC-C9-10 | **** | ≥100 |
| MSC-C10-10 | *** | ≥100 |
| MSB-C11-7 | *** | ≥100 |
| MSC-C10-11 | *** | ≥100 |

TABLE 9-continued

| | | |
|---|---|---|
| VDJA-C13-20 | *** | ≥100 |
| LSA-C9-32 | *** | ≥100 |
| MJA-C13-8 | ** | ≥100 |
| MSB-C13-8 | ** | ≥100 |
| MSC-C10-36 | **** | * |
| MSB-C13-16 | *** | * |
| MSC-C10-31 | *** | * |
| VDJA-C13-6 | *** | * |
| MSC-C15-8 | *** | * |
| MSC-C9-18 | *** | * |
| HTA-C9-16 | *** | ** |
| HTA-C9-17 | ** | * |

$IC_{50}$ value in the range ($\mu mol \cdot l^{-1}$)
≤10 $\mu mol \cdot l^{-1}$     ****
11-25 $\mu mol \cdot l^{-1}$   ***
26-50 $\mu mol \cdot l^{-1}$   **
≥51 $\mu mol \cdot l^{-1}$     *
≥100 $\mu mol \cdot l^{-1}$    ≥100

Canines, Reagents, Software and Instruments Used

Cell Lines:
CCRF-CEM (cat. no. CCL-119, ATCC/LGS Standards—American Type Cell Collection)
HUVEC (cat. no. 354151, BD Biosciences, USA)
HGC-27 (cat. no. 94042256, Sigma-Aldrich, USA)

Reagents:
Cell Cultivation:
Minimum Essential Medium Eagle (cat. no. M2279, Sigma-Aldrich, USA)
RPMI-1640 medium (cat. no. R7509, R7638 a R8758, Sigma-Aldrich, USA)
Dulbecco's Phosphate Buffered Saline (cat. no. D8537, Sigma-Aldrich, USA)
Penicillin-Streptomycin (cat. no. P0781, Sigma-Aldrich, USA)
Fetal bovine serum (cat. no. F9665, Sigma-Aldrich, USA)
L-glutamine, solution (cat. no. G7513, Sigma-Aldrich, USA)
MEM Non-essential Amino Acid Solution (cat. no. M7145, Sigma-Aldrich, USA)
0.25% trypsin-EDTA solution (cat. no. T4049, Sigma-Aldrich, USA)
Cultivation medium for HUVEC E-STIM™ (cat. no. 355054, BD Biosciences, USA)
Petri dishes coated with collagen I (cat. no. 354450, BD Biosciences, USA)

Transfection of Cells and Luciferase Reporter Analysis
Dual-Luciferase® Reporter Assay System (cat. no. E1960, Promega, USA)
pGL4.10 (luc2) Vector (cat. no. E665A, Promega, USA)
pRL-TK Vector (cat. no. E2241, Promega, USA)
X-tremeGENE HP DNA transfection agent (cat. no. 06366236001, Roche, Switzerland)
Opti-MEMS I Reduced Serum Medium (cat. no. 31985-062, Life Technologies, USA)
96-well plate Nunclon Delta Surface MicroWell Plates (cat. no. 136101, Thermo Fisher Scientific, Inc., USA)
Qiagen Plasmid Mini Kit (100) (cat. no. 12125, Qiagen, Nemecko)
Qiagen Plasmid Midi Kit (25) (cat. no. 12143, Qiagen, Nemecko)

Western Blot
Protease Inhibitor Cocktail—PrIC—(cat. no. P8340, Sigma-Aldrich, USA)
Halt Phosphatase Inhibitor Cocktail—PhIC (cat. no. 78420, Thermo Fisher Scientific, Inc., USA)
QuantiPro™ BCA Assay Kit (cat. no. QPBCA, Sigma-Aldrich, USA)
Immobilon-P Membrane (cat. no. IPVH00010, EMD Millipore Corporation, USA)
Mouse Monoclonal anti-MYC antibody (cat. no. 11-433-C100, EXBIO, Praha)
Anti-mouse IgG, HRP-konjugovaná protilátka (cat. no. 7076, Cell Signaling Technology, Inc., USA)
Monoclonal anti-β-Actin antibody (cat. no. A5441, Sigma-Aldrich, USA)
SuperSignal® West Femto Maximum Sensitivity Substrate (cat. no. 34095, Thermo Fisher Scientific, Inc., USA)
Nonfat Dry Milk (cat. no. 9999, Cell Signaling Technology, Inc., USA)
SignalBoost™ Immunoreaction Enhancer Kit (cat. no. 407207, EMD Millipore Corporation, USA)

XTT Assay
PMS (cat. no. P9625, Sigma-Aldrich, USA)
XTT (cat. no. X4626, Sigma-Aldrich, USA)

Software:
Microsoft Excel 2010 (Microsoft, USA)
Quantity One software V.4.6.9 (Bio-Rad, USA).
GraphPad Prism 5 V.5.04. (GraphPad Software, USA)

Instruments:
EnSpire Alpha Plate Reader (cat. no. 2300-001A, Perkin Elmer, USA)
ImageQuant LAS 4000 mini (cat. no. 28-9558-13, GE Healthcare Life Sciences, USA)
Fastblot B33 (cat. no. 014-100, Biometra, Německo)
Opticon 2 (cat. no. 200232, MJ Research, USA)

INDUSTRIAL APPLICABILITY

New helquats with heteroaromatic substituents can be used for the preparation of medicaments for treatment of diseases related to increased cellular proliferation and for stabilization of G-quadruplexes.

The invention claimed is:

1. A helquat derivative of the general formula I

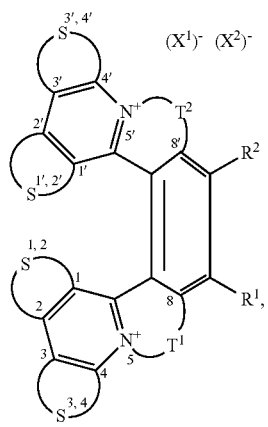

or its pharmaceutically acceptable salt, wherein $R^1$ and $R^2$ are independently selected from the group consisting of H and $C_1$ to $C_4$ alkyl;

up to three of $S^{1,2}$, $S^{1',2'}$, $S^{3,4}$ and $S^{3',4'}$ linkers are present, each of $S^{1,2}$, $S^{1',2'}$, $S^{3,4}$ and $S^{3',4'}$ independently represents a linker consisting of a bivalent hydrocarbon chain having 3-6 carbon atoms, or $S^{1,2}$, $S^{1',2'}$, $S^{3,4}$ and $S^{3',4'}$ are not present; and from one to four atoms selected from the carbon atoms with the descriptor 2, 4, 2', and 4' are substituted with a substituent $R^3$ of general formula II

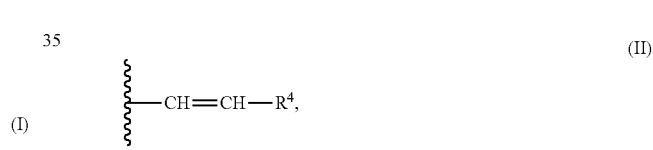

wherein $R^4$ is substituted or unsubstituted heteroaryl, $T^1$ and $T^2$ are independent linkers that bridge atoms $N^5$ with $C^8$ and $N^{5'}$ with $C^{8'}$, wherein $T^1$ and $T^2$ independently represent a bivalent hydrocarbon chain having 2-5 carbon atoms, wherein heteroaryl is an aromatic carbocyclic group containing:

4 to 26 carbon atoms, and at least one aromatic ring or multiple aromatic rings, wherein at least one carbon atom of the ring is replaced with a heteroatom selected from a group consisting of N, S and O; the heteroaryl can be unsubstituted or substituted with 1 to 5 substituents selected from a group consisting of $C_1$ to $C_6$ alkyl, $C_3$ to $C_{12}$ cycloalkyl optionally having at least one carbon atom of the ring replaced with a heteroatom selected from a group consisting of N, S and O; $C_6$ to $C_{16}$ aryl, $C_6$ to $C_{26}$ arylalkyl, $C_1$ to $C_6$ halogenoalkyl, $C_1$ to $C_{12}$ alkoxy, $C_6$ to $C_{16}$ aryloxy, benzyloxy, $C_1$ to $C_6$ alkylthio, $C_6$ to $C_{16}$ arylthio, halogeno, —OH, —SH, —$NH_2$, $C_1$ to $C_6$ alkylamino, $C_6$ to $C_{16}$ arylamino, $C_1$ to $C_6$ acylamino, —CN, nitro, —$SO_3H$ and —$COOR_n$, —C(=O)N($R_n$)$_2$, wherein $R_n$ is hydrogen or $C_1$ to $C_6$ alkyl or $C_6$ to $C_{16}$ $C_6$ to $C_{12}$aryl;

and anions $(X^1)^-$ and $(X^2)^-$ independently represent anions of salts.

2. The helquat derivative of the general formula I according to claim 1, wherein each of $S^{1,2}$, $S^{1',2'}$, $S^{3,4}$ and $S^{3',4'}$ independently represents a linker consisting of a bivalent hydrocarbon chain having 4 carbon atoms.

3. The helquat derivative of the general formula I according to claim 1, wherein each of $S^{1,2}$, $S^{1',2'}$, $S^{3,4}$ and $S^{3',4'}$ independently represents a linker consisting of a bivalent hydrocarbon chain having 4 carbon atoms and two double bonds.

4. The helquat derivative of the general formula I according to claim 1, wherein $T^1$ and $T^2$ independently represent a bivalent hydrocarbon chain having 2 or 3 carbon atoms.

5. The helquat derivative of the general formula I according to claim 1, wherein heteroaryl is an aromatic carbocyclic group containing 4 to 12 carbon atoms wherein at least one carbon atom of the ring is replaced with N, S, or O.

6. The helquat derivative of the general formula I according to claim 1, wherein anions $(X^1)^-$ and $(X^2)^-$ independently represent anions of pharmaceutically acceptable salts.

7. The helquat derivative of general formula I according to claim 1 selected from:
- 2,4-bis((E)-2-(thiophen-3-yl)vinyl)-6,7,10,11-tetrahydrodipyrido[2,1-a:1',2'-k][2,9]phenanthroline-5,12-diium trifluoromethanesulfonate,
- (E)-2-(2-(dibenzo[b,d]furan-4-yl)vinyl)-6,7,10,11-tetrahydrodipyrido[2,1-a:1',2'-k][2,9]phenanthroline-5,12-diium trifluoromethanesulfonate,
- (E)-13-(2-(5-(ethoxycarbonyl)-1H-pyrrol-3-yl)vinyl)-6,7-dimethyl-4,5,8,9-tetrahydroisoquinolino[1,2-a]pyrido[1,2-k][2,9]phenanthroline-3,10-diium trifluoromethanesulfonate,
- (E)-13-(2-(5-bromo-1H-indol-3-yl)vinyl)-6,7-dimethyl-4,5,8,9-tetrahydroisoquinolino[1,2-a]pyrido[1,2-k][2,9]phenanthroline-3,10-diium trifluoromethanesulfonate,
- 2,13-bis((E)-2-(5-bromothiophen-2-yl)vinyl)-8,9-dimethyl-6,7,10,11-tetrahydrodipyrido[2,1-a:1',2'-k][2,9]phenanthroline-5,12-diium trifluoromethanesulfonate,
- 2,13-bis((E)-2-(2,6-dimethoxypyridin-3-yl)vinyl)-8,9-dimethyl-6,7,10,11-tetrahydrodipyrido[2,1-a:1',2'-k][2,9]phenanthroline-5,12-diium trifluoromethanesulfonate,
- 19-((E)-2-(1-methyl-1H-indol-2-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate,
- 19-((E)-2-(2-methyl-1H-indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate,
- 19-((E)-2-(1H-benzo[g]indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate,
- 19-((E)-2-(2-phenyl-1H-indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate,
- 19-((E)-2-(1H-indol-5-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate,
- 19-((E)-2-(5-bromo-1H-indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate,
- 4,15-bis((E)-4-(pyridin-2-yl)styryl)-6,7,8,11,12,13-hexahydrodipyrido[1,2-a:1',2'-a']benzo[2,1-c:3,4-c']bisazepindiium trifluoromethanesulfonate,
- 2,4,15,17-tetra((E)-(2-(1-methyl-1H-indol-2-yl)vinyl)-6,7,8,11,12,13-hexahydrodipyrido[1,2-a:1',2'-a']benzo[2,1-c:3,4-c']bisazepindiium trifluoromethanesulfonate,
- (E)-11-(2-([2,2':5',2''-terthiophen]-5-yl)vinyl)-6,7-dimethyl-4,5,8,9-tetrahydroisoquinolino[1,2-a]pyrido[1,2-k][2,9]phenanthroline-3,10-diium trifluoromethanesulfonate,
- (E)-11-(2-(dibenzo[b,d]furan-4-yl)vinyl)-6,7-dimethyl-4,5,8,9-tetrahydroisoquinolino[1,2-a]pyrido[1,2-k][2,9]phenanthroline-3,10-diium trifluoromethanesulfonate,
- 2,15-bis((E)-2-(2,6-dimethoxypyridin-3-yl)vinyl)-6,7,10,11-tetrahydrodipyrido[2,1-a:1',2'-k][2,9]phenanthroline-5,12-diium trifluoromethanesulfonate,
- (E)-2-(2-(5-bromo-1H-indol-3-yl)vinyl)-6,7,10,11-tetrahydrodipyrido[2,1-a:1',2'-k][2,9]phenanthroline-5,12-diium trifluoromethanesulfonate,
- (E)-13-(2-(dibenzo[b,d]furan-4-yl)vinyl)-4,5,8,9-tetrahydroisoquinolino[1,2-a]pyrido[1,2-k][2,9] phenanthroline-3,10-diium trifluoromethanesulfonate,
- 2,15-bis((E)-2-(2-methyl-1H-indol-3-yl)vinyl)-6,7,10,11-tetrahydrodipyrido[2,1-a:1',2'-k][2,9]phenanthroline-5,12-diium trifluoromethanesulfonate,
- 2,15-bis((E)-2-(1-methyl-1H-indol-3-yl)vinyl)-6,7,10,11-tetrahydrodipyrido[2,1-a:1',2'-k][2,9]phenanthroline-5,12-diium trifluoromethanesulfonate,
- 2,15-bis((E)-2-(2-phenyl-1H-indol-3-yl)vinyl)-6,7,10,11-tetrahydrodipyrido[2,1-a:1',2'-k][2,9]phenanthroline-5,12-diium trifluoromethanesulfonate,
- 2,15-bis((E)-2-(5-bromo-1H-indol-3-yl)vinyl)-6,7,10,11-tetrahydrodipyrido[2,1-a:1',2'-k][2,9]phenanthroline-5,12-diium trifluoromethanesulfonate,
- (rac)-(E)-13-(2-(dibenzo[b,d]furan-4-yl)vinyl)-6,7-dimethyl-4,5,8,9-tetrahydroisoquinolino[1,2-a]pyrido[1,2-k][2,9]phenanthroline-3,10-diium trifluoromethanesulfonate,
- 8,9-dimethyl-2,15-bis((E)-2-(2-methyl-1H-indol-3-yl)vinyl)-6,7,10,11-tetrahydrodipyrido[2,1-a:1',2'-k][2,9]phenanthroline-5,12-diium trifluoromethanesulfonate,
- 2,15-bis((E)-2-(1H-pyrrolo[2,3-b]pyridin-3-yl)vinyl)-8,9-dimethyl-6,7,10,11-tetrahydrodipyrido[2,1-a:1',2'-k][2,9]phenanthroline-5,12-diium trifluoromethanesulfonate,
- 2,4-bis((E)-2-(1H-indol-2-yl)vinyl)-6,7,10,11-tetrahydrodipyrido[2,1-a:1',2'-k][2,9]phenanthroline-5,12-diium trifluoromethanesulfonate,
- 2,4-bis((E)-2-([2,2'-bithiophen]-5-yl)vinyl)-6,7,10,11-tetrahydrodipyrido[2,1-a:1',2'-k][2,9]phenanthroline-5,12-diium trifluoromethanesulfonate,
- 2,4-bis((E)-2-(benzofuran-2-yl)vinyl)-6,7,10,11-tetrahydrodipyrido[2,1-a:1',2'-k][2,9]phenanthroline-5,12-diium trifluoromethanesulfonate,
- (E)-2-(2-([2,2'-bithiophen]-5-yl)vinyl)-6,7,10,11-tetrahydrodipyrido[2,1-a:1',2'-k][2,9]phenanthroline-5,12-diium trifluoromethanesulfonate,
- (E)-13-(2-(5-hexylthiophen-2-yl)vinyl)-6,7-dimethyl-4,5,8,9-tetrahydroisoquinolino[1,2-a]pyrido[1,2-k][2,9]phenanthroline-3,10-diium trifluoromethanesulfonate,
- (E)-13-(4-(9H-carbazol-9-yl)styryl)-6,7-dimethyl-4,5,8,9-tetrahydroisoquinolino[1,2-a]pyrido[1,2-k][2,9]phenanthroline-3,10-diium trifluoromethanesulfonate,
- 8,9-dimethyl-2,13-bis((E)-2-(4-methyl-1H-imidazol-5-yl)vinyl)-6,7,10,11-tetrahydrodipyrido[2,1-a:1',2'-k][2,9]phenanthroline-5,12-diium trifluoromethanesulfonate, 19-((E)-2-(3-methylbenzo[b]thiophen-2-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, 19-((E)-2-([2,2'-bithiophen]-5-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, 19-((E)-2-(6-bromo-1H-indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, 2,15-bis((E)-2-(4-methyl-1H-imidazol-5-yl)vinyl)-6,7,10,11-tetrahydrodipyrido[2,1-a:1',2'-k][2,9] phenanthroline-5,12-diium trifluoromethanesulfonate, 2,15-bis((E)-2-(dibenzo[b,d]furan-4-yl)vinyl)-8,9-dimethyl-6,7,10,11-tetrahydrodipyrido[2,1-a:1',2'-k][2,9]phenanthroline-5,12-diium trifluoromethanesulfonate, (rac)-2,4,13,15-tetrakis((E)-2-(thiophen-3-yl)vinyl)-6,7,8,11,12,13-hexahydro-dipyrido[1,2-a;1',2'-a']benzo[2,1-c:3,4-c']bisazepindiium trifluoromethanesulfonate, (E)-13-(2-(dibenzo[b,d]furan-2-yl)vinyl)-6,7-dimethyl-4,5,8,9-tetrahydroisoquinolino[1,2-a]pyrido[1,2-k][2,9]phenanthroline-3,10-diium trifluoromethanesulfonate, (E)-13-(2-(4-phenylthiophen-2-yl)vinyl)-4,5,8,9-tetrahydroisoquinolino[1,2-a]pyrido[1,2-k][2,9] phenanthroline-3,10-diium trifluoromethanesulfonate, (E)-13-(2-(1H-benzo[g]indol-3-yl)vinyl)-4,5,8,9-tetrahydroisoquinolino[1,2-a]pyrido[1,2-k][2,9] phenanthroline-3,10-diium trifluoromethanesulfonate, 19-((E)-2-(7-methyl-1H-indol-3-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate, (E)-11-(2-(dibenzo[b,d]thiophen-4-yl)vinyl)-6,7-dimethyl-4,5,8,9-tetrahydroisoquinolino[1,2-a]pyrido[1,2-k][2,9]phenanthroline-3,10-diium trifluoromethanesulfonate, (rac)-(E)-13-(2-(9-ethyl-9H-carbazol-3-yl)vinyl)-6,7-dimethyl-4,5,8,9-tetrahydroisoquinolino[1,2-a]pyrido[1,2-k][2,9]phenanthroline-3,10-diium trifluoromethanesulfonate, (rac)-8,9-dimethyl-2,13-bis((E)-2-(thiophen-3-yl)vinyl)-6,7,10,11-tetrahydrodipyrido[2,1-a:1',2'-k][2,9] phenanthroline-5,12-diium trifluoromethanesulfonate, (rac)-2,15-bis((E)-2-(1H-indol-3-yl)vinyl)-6,7,8,11,12,13-hexahydrodipyrido[1,2-a:1',2'-a']benzo[2,1-c:3,4-c']bisazepindiium trifluoromethanesulfonate, 4,13-bis((E)-2-(2-methyl-1H-indol-3-yl)vinyl)-6,7,10,11-tetrahydrodipyrido[2,1-a:1',2'-k][2,9]phenanthroline-5,12-diium trifluoromethanesulfonate, (E)-11-(2-(benzo[d]thiazol-2-yl)vinyl)-6,7-dimethyl-4,5,8,9-tetrahydroisoquinolino[1,2-a]pyrido[1,2-k][2,9] phenanthroline-3,10-diium trifluoromethanesulfonate, (E)-6,7-dimethyl-11-(2-(5-phenylthiophen-2-yl)vinyl)-4,5,8,9-tetrahydroisoquinolino[1,2-a]pyrido[1,2-k][2,9] phenanthroline-3,10-diium trifluoromethanesulfonate, (rac)-(E)-2-(2-(4-nitro-1H-indol-3-yl)vinyl)-6,7,10,11-tetrahydrodipyrido[2,1-a:1',2'-k][2,9]phenanthroline-5,12-diium trifluoromethanesulfonate, (rac)-(E)-2-(2-(6-isopropyl-1H-indol-3-yl)vinyl)-6,7,8,11,12,13-hexahydrodipyrido[1,2-a:1',2'-a']benzo[2,1-c:3,4-c']bisazepindiium trifluoromethanesulfonate, (rac)-2,17-bis((E)-2-(1H-indol-5-yl)vinyl)-6,7,8,11,12,13-hexahydrodipyrido[1,2-a:1',2'-a']benzo[2,1-c:3,4-c']bisazepindiium trifluoromethanesulfonate, (rac)-4,15-bis((E)-2-(2,5-dimethyl-1-(3-(trifluoromethyl)phenyl)-1H-pyrrol-3-yl)vinyl)-6,7,8,11,12,13-hexahydrodipyrido[1,2-a:1',2'-a']benzo[2,1-c:3,4-c']bisazepindiium trifluoromethanesulfonate, 8,9-dimethyl-2,15-bis((E)-2-(2-phenyl-1H-indol-3-yl)vinyl)-6,7,10,11-tetrahydrodipyrido[2,1-a:1',2'-k][2,9] phenanthroline-5,12-diium trifluoromethanesulfonate, (rac)-2,4,15,17-tetrakis((E)-2-(1H-indol-2-yl)-6,7,8,11,12,13-hexahydro-dipyrido[1,2-a;1',2'-a']benzo[2,1-c:3,4-c']bisazepindiium trifluoromethanesulfonate, (rac)-2,4-bis((E)-2-(1-methyl-1H-pyrrol-2-yl)vinyl)-6,7,10,11-tetrahydro-dipyrido[2,1-a:1',2'-k][2,9]phenanthroline-5,12-diium trifluoromethanesulfonate, (rac)-2,4-bis((E)-2-(4-methyl-1H-imidazol-5-yl)vinyl)-6,7,10,11-tetrahydro-dipyrido[2,1-a:1',2'-k][2,9]phenanthroline-5,12-diium trifluoromethanesulfonate, 2,4,13,15-tetrakis((E)-2-(1-methyl-1H-indol-3-yl)vinyl)-6,7,10,11-tetrahydrodipyrido[2,1-a:1',2'-k][2,9] phenanthroline-5,12-diium trifluoromethanesulfonate.

8. The helquat derivative of general formula I according to claim 1 or its pharmaceutically acceptable salt for use as medicaments.

9. The helquat derivative of general formula I according to claim 1 or its pharmaceutically acceptable salt for use in stabilization of G-quadruplexes.

10. The helquat derivative of general formula I according to claim 1 or its pharmaceutically acceptable salt for use in treating cancer by stabilizing G-quadruplex.

11. The helquat derivative of general formula I according to claim 1 or its pharmaceutically acceptable salt for use in treating cancer by stabilizing G-quadruplex.

12. The helquat derivative of general formula I according to claim 1 or its pharmaceutically acceptable salt for use as medicaments in treating cancer by stabilizing G-quadruplex at telomeres or in gene promoters.

13. The helquat derivative according to claim 7 or its pharmaceutically acceptable salt for use as medicaments in treating cancer by stabilizing G-quadruplex at telomeres or in gene promoters.

14. A pharmaceutical preparation, containing at least one helquat derivative of general formula I according to claim 1 or its pharmaceutically acceptable salt.

15. The pharmaceutical preparation according to claim 7, which further contains at least one pharmaceutically acceptable carrier, filler, or diluent and optionally another active ingredient.

16. The pharmaceutical preparation according to claim 14 for use in treating cancer by stabilizing G-quadruplex.

17. A pharmaceutical preparation according to claim 2 for use in treating cancer by stabilizing of G-quadruplex at telomeres or in gene promoters.

18. A method of treating cancer by stabilizing G-quadruplex comprising the step of administering helquat derivatives of general formula I according to claim 1 or its pharmaceutically acceptable salt.

19. A method treating cancer by stabilizing G-quadruplex at telomeres or in gene promoters, comprising the step of administering a helquat derivative of general formula I according to claim 1 or its pharmaceutically acceptable salt.

20. A method of treating cancer by stabilizing G-quadruplex comprising the step of administering a helquat according to claim 7 or its pharmaceutically acceptable salt.

21. A method treating cancer by stabilizing G-quadruplex at telomeres or in gene promoters, comprising the step of administering helquats according to claim 7 or its pharmaceutically acceptable salt.

* * * * *